(12) United States Patent
Ravetch

(10) Patent No.: US 7,416,726 B2
(45) Date of Patent: Aug. 26, 2008

(54) ENHANCEMENT OF ANTIBODY-MEDIATED IMMUNE RESPONSES

(75) Inventor: Jeffrey V. Ravetch, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/834,321

(22) Filed: Apr. 13, 2001

(65) Prior Publication Data

US 2001/0036459 A1 Nov. 1, 2001

Related U.S. Application Data

(60) Provisional application No. 60/198,550, filed on Apr. 13, 2000, provisional application No. 60/204,254, filed on May 15, 2000.

(51) Int. Cl.
*A61K 39/395* (2006.01)
*A61K 39/40* (2006.01)
(52) U.S. Cl. .............. 424/133.1; 424/141.1; 424/155.1; 424/156.1
(58) Field of Classification Search .............. 424/133.1, 424/141.1, 155.1, 156.1
See application file for complete search history.

(56) References Cited

U.S. PATENT DOCUMENTS

| | | | |
|---|---|---|---|
| 4,752,601 A | 6/1988 | Hahn | 514/14 |
| 4,816,567 A | 3/1989 | Cabilly et al. | 530/387 |
| 4,946,778 A | 8/1990 | Ladner et al. | 435/69.6 |
| 5,034,506 A | 7/1991 | Summerton et al. | 528/391 |
| 5,132,405 A | 7/1992 | Huston et al. | 530/387.3 |
| 5,348,876 A | 9/1994 | Michaelsen et al. | 435/240.2 |
| 5,459,127 A | 10/1995 | Felgner et al. | 514/7 |
| 5,476,786 A | 12/1995 | Huston | 435/252.33 |
| 5,554,601 A | 9/1996 | Simpkins et al. | 514/182 |
| 5,580,859 A | 12/1996 | Felgner et al. | 514/44 |
| 5,589,466 A | 12/1996 | Felgner et al. | 514/44 |
| 5,624,821 A | 4/1997 | Winter et al. | 435/69.6 |
| 5,637,687 A | 6/1997 | Wiggins | 536/23.1 |
| 5,648,260 A | 7/1997 | Winter et al. | 435/252.3 |
| 5,677,437 A | 10/1997 | Teng et al. | 536/23.1 |
| 5,698,449 A | 12/1997 | Baumann et al. | 436/507 |
| 5,736,137 A | 4/1998 | Anderson et al. | 424/133.1 |
| 5,773,231 A | 6/1998 | Medford et al. | 435/7.24 |
| 5,780,607 A | 7/1998 | Goodnow, Jr. et al. | 536/22.1 |
| 5,783,682 A | 7/1998 | Cook et al. | 536/24.3 |
| 5,792,844 A | 8/1998 | Sanghvi et al. | 536/23.1 |
| 5,811,234 A | 9/1998 | Roninson et al. | 435/6 |
| 5,814,500 A | 9/1998 | Dietz | 435/172.3 |
| 5,834,597 A | 11/1998 | Tso et al. | 530/387.3 |
| 5,981,216 A | 11/1999 | Masure et al. | 435/69.3 |
| 5,985,599 A | 11/1999 | McKenzie et al. | 435/69.1 |
| 6,025,198 A | 2/2000 | Bennett et al. | 435/375 |
| 6,028,053 A | 2/2000 | van der Geer et al. | 514/7 |
| 6,194,551 B1 | 2/2001 | Idusogie et al. | 530/387.1 |

FOREIGN PATENT DOCUMENTS

| | | |
|---|---|---|
| CA | 2012311 | 9/1990 |
| WO | WO 86/01533 | 3/1986 |
| WO | WO 88/07089 | 9/1988 |
| WO | WO 89/07142 | 8/1989 |
| WO | WO 92/05263 | 4/1992 |
| WO | WO 94/21807 | 9/1994 |
| WO | WO 94/29351 | 12/1994 |
| WO | WO 95/05468 | 2/1995 |
| WO | WO 95/18863 | 7/1995 |
| WO | WO 95/21931 | 8/1995 |
| WO | WO 95/28494 | 10/1995 |
| WO | WO 96/17823 | 6/1996 |
| WO | WO 96/25508 | 8/1996 |
| WO | WO 97/28267 | 8/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/01157 | 1/1999 |
| WO | WO 99/01158 | 1/1999 |
| WO | WO 99/01175 | 1/1999 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 00/15214 | 3/2000 |

OTHER PUBLICATIONS

Colman et al., Research in Immunology (145(1):33-36, 1994.*
Abaza et al., Journal of Protein Chemistry (11(5):433-444, 1992.*

(Continued)

*Primary Examiner*—Michail A Belyavskyi
(74) *Attorney, Agent, or Firm*—Pepper Hamilton LLP

(57) ABSTRACT

The present invention is related to enhancing the function of anti-tumor antibodies by regulating FcγRIIB-mediated activity. In particular, disrupting SHIP activation by FcγRIIB enhances cytotoxicity elicited by a therapeutic antibody in vivo in a human. The invention further provides an antibody, e.g., an anti-tumor antibody, with a variant Fc region that results in binding of the antibody to FcγRIIB with reduced affinity. A variety of transgenic mouse models demonstrate that the inhibiting FcγRIIB molecule is a potent regulator of cytotoxicity in vivo.

41 Claims, 3 Drawing Sheets

OTHER PUBLICATIONS

Lederman et al Molecular Immunology (28:1171-1181, 1991.*
Li et al PNAS 77:3211-3214, 1980.*
Ngo et al., The Protein Folding Problem and Tertiary Structure Prediction, 1994, Merz et al., (ed.), Birkhauser, Boston, MA, pp. 433 and 492-495.*
Pearse et al., Immunol., 1999, vol. 10, pp. 753-760.*
Gupta, N., et al., "Negative signaling pathways of the killer cell inhibitory receptor and FcγIIb1 require distinct phosphatases," *J. Experimental Medicine*, 1997, 186(3), 473-478.
Baselga, J., et al., "Recombinant humanized anti-HER2 antibody (Herceptin™) enhances the antitumor activity of paclitaxel and doxorubicin against HER2/neu overexpressing human breast cancer xenografts," *Cancer Res.*, Jul. 1, 1998, 58, 2825-2831.
Bird, R.E., et al., "Single-chain antigen-binding proteins," *Science*, Oct. 21, 1988, 242, 423-426.
Boder, E.T., et al., "Yeast surface display for screening combinatorial polypeptide libraries," *Nat. Biotechnol.*, Jun. 1997, 15, 553-557.
Bolland, S., et al., "SHIP modulates immune receptor responses by regulating membrane association of Btk," *Immunity*, Apr. 1998, 8, 509-516.
Brooks, D.G., et al., "Structure and expression of human IgG FcRII(CD32) functional heterogeneity is encoded by the alternatively spliced products of multiple genes," *J. Exp. Med.*, Oct. 1989, 170, 1369-1385.
Buchwald, H., et al., "Long-term, continuous intravenous heparin administration by an implantable infusion pump in the ambulatory patients with recurrent venous thrombosis," *Surgery*, Oct. 1980, 88(4), 507-516.
Burton, D.R., "Immunoglobulin G: functional sites," *Mol. Immunol.*, 1985, 22(3), 161-206.
Capel, P.J.A., et al., "Heterogeneity of human IgG Fc receptors," *Immunomethods*, 1994, 4, 25-34.
Carter, P., et al., "Humanization of an anti-p185$^{HER2}$ antibody for human cancer therapy," *Proc. Natl. Acad. Sci. USA*, May 1992, 89, 4285-4289.
Clackson, T., et al., "Making antibody fragments using phage display libraries," *Nature*, Aug. 15, 1991, 352, 624-628.
Cochet, O., et al., "Intracellular expression of an antibody fragment-neutralizing p21 Ras promotes tumor regression," *Cancer Res.*,Mar. 15, 1998, 58, 1170-1176.
Cox, A.L., et al., "Identification of a peptide recognized by five melanoma-specific human cytotoxic T cell lines," *Science*, Apr. 29, 1994, 264, 716-719.
Curiel, D.T., et al., "High-efficiency gene transfer mediated by adenovirus coupled to DNA-polylysine complexes," *Hum. Gene Ther.*, 1992, 3, 147-154.
Curiel, D.T., "Targeted tumor cytotoxicity mediated by intracellular single-chain anti-oncogene antibodies," Gene Therapy Program, *Advances in Pharmacology*, 1997, 40, 51-84.
Daëron, M., "Fc receptor biology," *Annu. Rev. Immunol.*, 1997, 15, 203-234.
Damen, "The 145-kDa protein induced to associate with Shc by multiple cytokines is an inositol tetraphosphate and phosphatidylinositol 3,4,5-triphosphate 5-phosphatase," *Proc. Natl. Acad. Sci. USA*, 1996, 93, 1681693.
de Haas, M., et al., "Fcγ receptors of phagocytes," *J. Lab. Clin. Med.*, 1995, 126, 330-341.
Deisenhofer, J., "Crystallographic refinement and atomic models of a human Fc fragment and its complex with fragment B of protein A from *Staphylococcus aureus* at 2.9- and 2.8-Å resolution," *Am. Chem. Soc.*, Apr. 28, 1981, 20(9), 2361-2370.
During, M.J., et al., "Controlled release of dopamine from a polymeric brain implant: in vivo characterization," *Ann. Neurol.*, 1989, 25, 351-356.
Ellman, J., et al., "Biosynthetic method for introducing unnatural amino acids site-specifically into proteins," *Meth. In Enzym.*, 1991, 202, 301-336.
Felgner, P.L., et al., "Cationic liposome-mediated transfection," *Nature*, Jan. 26, 1989, 337, 387-388.
Felgner, P.L., et al., "Lipofection: a highly efficient, lipid-mediated DNA-transfection procedure," *Proc. Natl. Acad. Sci. USA*, Nov. 1987, 84, 7413-7417.
Goodson, J.M., in *Medical Applications of Controlled Release*, 1984, vol. 2, 115-138.
Han, D.C., et al., "Therapy with antisense TGF-β1 oligodeoxynucleotides reduces kidney weight and matrix mRNAs in diabetic mice," *Am. J. Physiol. Renal Physiol.*, 2000, 278, F628-F634.
Hanna, A.K., et al., "Adenoviral-mediated expression of antisense RNA to basic fibroblast growth factor reduces tangential stress in arterialized vein grafts," *J. Vasc. Surg.*, 2000, 31, 770-780.
Howard, M.A., et al., "Intracerebral drug delivery in rats with lesion-induced memory deficits," *J. Neurosurg.*, 1989, 71, 105-112.
Huse, W.D., et al., "Generation of a large combinatorial library of the immunoglobulin repertoire in phage lambada," *Science*, Dec. 8, 1989, 246, 1275-1281.
Huston, J.S., et al., Protein engineering of antibody binding sites: recovery of specific activity in an anti-digoxin single-chain Fv analogue produced in *Escherichia coli*, *Proc. Natl. Acad. Sci. USA*, Aug. 1988, 85, 5879-5883.
Jerome, K.R., et al., "Cytotoxic T-lymphocytes derived from patients with breast adenocarcinoma recognized an epitope present on the protein core of a mucin molecule preferentially expressed by malignant cells," *Cancer Res.*, Jun. 1, 1991, 51, 2908-2916.
Jones, P.T., et al., "Replacing the complementarity-determining regions in a human antibody with those from a mouse," *Nature*, May 29, 1986, 321, 522-525.
Kaplitt, M.G., et al., "Expression of a functional foreign gene in adult mammalian brain following in vivo transfer via a herpes simplex virus type 1 defective viral vector," *Mol. & Cell. Neurosci.*, 1991, 2, 320-330.
Kavanaugh, W.M., et al., "Multiple forms of an inositol polyphosphate 5-phosphatase form signaling complexes with Shc and Grb2," *Curr. Biol.*, 1996, 6(4), 438-445.
Köhler, G., et al., *Nature*, Aug. 7, 1975, 256, 495-497.
Kopreski, M.S., et al., "Growth inhibition of breast cancer cell lines by combinations of anti-P185$^{HER2}$ monoclonal antibody and cytokines," *Anticancer Res.*, 1996, 16, 433-436.
Langer, R., "New methods of drug delivery," *Science*, Sep. 28, 1990, 249, 1527-1533.
Langer, R., et al., "Chemical and physical structure of polymers as carriers for controlled release of bioactive agents: a review," *JMS-Rev. Macromol. Chem. Phys.*, 1983, C23(I), 61-126.
LaSalle, G.L., et al., "An adenovirus vector for gene transfer into neurons and glia in the brain," *Science*, Feb. 12, 1993, 259, 988-990.
Lebkowski, J.S., et al., "Adeno-associated virus: a victor system for efficient introduction and integration of DNA into a variety of mammalian cell types," *Mol. and Cell Biol.*, 1988, 8(10), 3988-3996.
Leget, G.A., et al., "Use of rituximab, the new FDA-approved antibody," *Curr. Opin. In Oncol.*, 1998, 10, 548-551.
Leung, D.W., et al., "A method for random mutagenesis of a defined DNA segment using a modified polymerase chain reaction," *Technique, J. Methods in Cell & Mol. Bio.*, Aug. 1989, 1(1), 11-15.
Levy, R.J., et al., "Inhibition of calcification of bioprosthetic heart valves by local controlled-release diphosphonate," *Science*, Apr. 12, 1985, 228, 190-192.
Lewis, G.D., et al., "Differential responses of human tumor cell lines to anti-p185$^{HER2}$ monoclonal antibodies," *Cancer Immunol. Immunother.*, 1993, 37, 255-263.
Lopez-Berestein, G., "Treatment of systemic fungal infections with liposomal-amphotericin B," in *Liposomal in the Therapy of Infectious Diseases and Cancer*, 1989, 317-327.
Liu, J., et al., "Characterization of complex formation by humanized anti-IgE monoclonal antibody and monoclonal human IgE," *Biochem.*, 1995, 34, 10474-10482.
Mack, A., et al., "The key role of butyrylcholinesterase during neurogenesis and neural disorders: an antisense-5'butyrylcholinesterase-DNA study," *Prog. Neurobiol.*, 2000, 60, 607-628.
Machy, P., et al., "Gene transfer from targeted liposomes to specific lymphoid cells by eletroporation," *Proc. Natl. Acad. Sci. USA*, Nov. 1988, 85, 8027-8031.

Marasco, W.A., et al., "Intracellular antibodies against HIV-1 envelope protein for AIDS gene therapy," *Hum. Gene Ther.*, Jul. 20, 1998, 9, 1627-1642.

Marks, J.D., et al., "By-passing immunization human antibodies from V-gene libraries displays on phage," *J. Mol. Biol.*, 1991, 222, 581-597.

Masui, H., et al., "Mechanism of antitumor activity in mice for anti-epidermal growth factor receptor monoclonal antibodies with different isotypes," *Cancer Res.*, Nov. 1986, 46, 5592-5598.

Miller, A.D., et al., "Improved retroviral vectors for gene transfer and expression," *BioTechnqiues*, 1989, 7(9), 980-990.

Mir, L.M., et al., "Long-term, high level in vivo gene expression after electric pulse-mediated gene transfer into skeletal muscle," *C.R. Acad. Sci. Paris*, 1998, 321, 893-899.

Morioka, N., et al., "A decapeptide (Gln-Asp-Leu-Thr-Met-Lys-Tyr-Gln-Ile-Phe) from human melanoma is recognized by CTL in melanoma patients," *J. Immunol.*, 1994, 153, 5650-5658.

Morrison, S.L., et al., "Chimeric human antibody molecules: mouse antigen-binding domains with human constant region domains," *Proc. Natl. Acad. Sci. USA*, Nov. 1984, 81, 6851-6855.

Neuberger, M.S., et al., "Recombinant antibodies possessing novel effector functions," *Nature*, Dec. 1984, 312, 604-608.

Nielsen, P.E., et al., "Sequence-selective recognition of DNA by strand displacement with a thymine-substituted polyamide," *Science*, Dec. 6, 1991, 254, 1497-1500.

Noren, C.J., et al., "A general method for site-specific incorporation of unnatural amino acids in proteins," *Science*, Apr. 14, 1989, 244, 182-188.

Ono, M., et al., "Role of the inositol phosphatase SHIP in negative regulation of the immune system by the receptor FcγR11B," *Nature*, Sep. 19, 1996, 383, 263-266.

Ono, M., et al., "Deletion of SHIP or SHP-1 reveals two distinct pathways for inhibitory signaling," *Cell*, Jul. 25, 1997, 90, 293-301.

Pegram, M.D., et al., "Phase II study of receptor-enhanced chemosensitivity using recombinant humanized anti-p185$^{HER2/neu}$ monoclonal antibody plus cisplatin in patients with HER2/neu-overexpressing metastatic breast cancer refractory to chemotherapy treatment," *J. Clin. Oncol.*, Aug. 1998, 16(8), 2659-2671.

Peoples, G.E., et al., "HLA-═A2 presents shared tumor-associated antigens derived from endogenous proteins in ovarian cancer," *J. Immunol.*, Nov. 15, 1993, 151(10), 5481-5491.

Prati, E.G.P., et al., "Engineering of coordinated up- and down-regulation of two glycosyltransferases of the O-Glycosylation pathway in chinese hamster ovary (CHO) cells," *Biotechnol. and Bioeng.*, May 5, 2000, 68(3), 239-244.

Presta,, L.G., "Antibody engineering," *Curr. Op. Struct. Biol.*, 1992, 2, 593-596.

Ravetch, J.V., et al., "Fc receptors," *Annu. Rev. Immunol.*, 1991, 9, 457-492.

Richardson, J.H., et al., "Intrabody-mediated knockout of the high-affinity IL-2 receptor in primary human T cells using a bicistronic lentivirus vector," *Gene Ther.*, 1998, 5, 635-644.

Riechmann, L., et al., "Reshaping human antibodies for therapy," *Nature*, Mar. 1988, 332, 323-327.

Sahasrabudhe, D.M., et al., "Shared T cell-defined antigens on independently derived tumors," *J. Immunol.*, Dec. 1, 1993, 151(11), 6302-6310.

Samulski, R.J., et al., "A recombinant plasmid from which an infectious adeno-associated virus genome can be excised in vitro and its use to study viral replication," *J. Virol.*, Oct. 1987, 61(10), 3096-3101.

Samulski, R.J., et al., "Helper-free stocks of recombinant adeno-associated viruses: normal integration does not require viral gene expression," *J. Virol.*, Sep. 1989, 63(9), 3822-3828.

Saudek, C.D., et al., "A preliminary trial of the programmable implantable medication system for insulin delivery," *N. Engl. J. Med.*, Aug. 31, 1989, 321(9), 574-579.

Saviranta, P., et al., "Engineering the steroid-specificity of an anti-17β-estradiol fab by random mutagenesis and competitive phage panning," *Prot. Eng.*, 1998, 11(2), 143-152.

Sefton, M.V., "Implantable pumps," *CRC Crit. Rev. Biomed. Eng.*, England, 1987, 14(3), 201-240.

Shamamian, P., et al., "Recognition of neuroectodermal tumors by melanoma-specific cytotoxic T lymphocytes: evidence for antigen sharing by tumors derived from the neural crest," *Cancer Immunol. Immunother*, 1994, 39, 73-83.

Shan, D., et al., "A poptosis of malignant human B cells by ligation of CD20 with monoclonal antibodies," *Blood*, Mar. 1, 1998, 91(5), 1644-1652.

Stratford-Perricaudet, L.D., et al., "Widespread long-term gene transfer to mouse skeletal muscles and heart," *J. Clin. Invest.*, Aug. 1992, 90, 626-630.

Taji, H., et al., "Growth inhibition of CD20-positive B lymphoma cell lines by IDEC-C2B8 anti-CD20 monoclonal antibody," *Jpn. J. Cancer Res.*, Jul. 1998, 89, 748-756.

Takai, T., et al., "Augmented humoral and anaphylactic responses in FcγR11-deficient mice," *Nature*, Jan. 25, 1996, 379, 346-349.

Takai, T., et al., "FcRγ chain deletion results in pleiotrophic effector cell defects," *Cell*, Feb. 11, 1994, 76, 519-529.

Takeda, S., et al., "Construction of chimaeric processed immunoglobulin genes containing mouse variable and human constant region sequences," *Nature*, Apr. 4, 1985, 314, 452-454.

Treat, J., et al., "Liposome encapsulated doxorubicin preliminary results of phase 1 and phase II trials," in *Liposomes in the Therapy of Infectious Disease and Cancer*, 1989, 353-365.

Tutt, A.L., et al., "Monoclonal antibody therapy of B cell lymphoma: signaling activity on tumor cells appears more important than recruitment of effectors," *J. Immunol.*, 1998, 161, 3176-3185.

Ulmer, J.B., et al., "Heterologous protection against influenza by injection of DNA encoding a viral protein," *Science*, Mar. 19, 1993, 259, 1745-1749.

Waldmann, T.A., "Lymphokine receptors: a target for immunotherapy of lymphomas," *Ann. Oncol.*, 1994, 5 Supp. I, S13-S17.

Ward, E.S., et al., "The effector functions of immunoglobulins: implications for therapy," *Therapeutic Immunol.*, 1995, 2, 77-94.

Ward, E.S., et al., "Binding activities of a repertoire of single immunoglobulin variable domains secreted from *Escherichia coli*," *Nature*, Oct. 12, 1989, 341, 544-546.

Williams, R.S., et al., "Introduction of foreign genes into tissues of living mice by DNA-coated microprojectiles," *Proc. Natl. Acad. Sci. USA*, Apr. 1991, 88, 2726-2730.

Wilson, J.M., "Hepatocyte-directed gene transfer in vivo leads to transient improvement of hypercholesterolemia in low density lipoprotein receptor-deficient rabbits," *J. Biol. Chem.*, Jan. 15, 1992, 267(2), 963-967.

Wu, G.Y., et al., "Receptor-mediated in vitro gene transformation by a soluble DNA carriers system," *J. Biol. Chem.*, Apr. 5, 1987, 262(10), 4429-4432.

Wu, G.Y., et al., "Receptor-mediated gene delivery and expression in vivo," *J. Biol. Chem.*, Oct. 15, 1988, 263(19), 14621-14624.

Yang, C., et al., "Antisense suppression of proline-directed protein kinase $F_A$ enhances chemosensitivity in human prostate," *Clin. Cancer Res.*, Mar. 2000, 6, 1024-1030.

Yang, L., et al., "Expression of *ERCC1* antisense rna abrogates gemcitabine-mediated cytotoxic synergism with cisplatin in human colon tumor cells defective in mismatch repair but proficient in nucleotide excision repair," *Clin. Cancer Res.*, Mar. 2000, 6, 773-781.

Yuan, R., et al., "Antibody-mediated modulation of *Cryptococcus neoformans* infection is dependent on distinct Fc receptor functions and IgG subclasses," *J. Exp. Med.*, Feb. 16, 1998, 187(4), 641-648.

Lin, S., et al., "Giving inhibitory receptors," *Science*, Jan. 19, 2001, 291, 445-446.

Samuelsson, A., et al., "Anti-inflammatory activity of IVIG mediated through the inhibitory Fc receptor," *Science*, Jan. 19, 2001, 291, 484-486.

Allan, R., et al. "Studies on the complement-binding site of rabbit immunoglobulin G-I. Modification of tryptophan residues and their role in anticomplementary activity of rabbit IgG" *Immunochemistry*, 1974, 11(4), 175-180.

Angal, S., et al., "A single amino acid substitution abolishes the heterogeneity of chimeric mouse/human (IgG4) antibody" *Molecular Immunology*, 1993, 30(1), 105-108.

Armour, K.L., et al., "Recombinant human IgG molecules lacking Fc\147 receptor I binding and monocyte triggering activities" *European Journal of Immunology*, 1999, 29(8), 2613-2624.

Bloom, J.W., et al., "Intrachain disulfide bond in the core hinge region of human IgG4" *Protein Science*, 1997, 6, 407-415.

Bredius, R.G.M., et al., "Role of neutrophil Fc\147\norRIIa (CD32) and Fc\147\norRIIIB (CD16) polymorphic forms in phagocytosis of human IgG1- and IgG3-opsonized bacteria and erythrocytes" *Immunology*, 1994, 83(4), 624-630.

Brekke, O.H., et al., "Human IgG isotype-specific amino acid residues affecting complement-mediated cell lysis and phagocytosis" *European Journal of Immunology*, 1994, 24(10), 2542-2547.

Burmeister, W.P., et al., "Crystal structure of the complex of rat neonatal Fc receptor with Fc" *Nature*, 1994, 372(6504), 379-383.

Burton, D.R., et al., "Molecular recognition of antibody (IgG) by cellular Fc receptor (FcRI)" *Molecular Immunology*, 1988, 25(11), 1175-1181.

Burton, D.R., et al., "The Clq receptor site on immunoglobulin G" *Nature*, 1980, 288(5789), 338-344.

Burton, D.R., "Human antibody effector function," *Advances in Immunol.*, 1992, 51, 1-84.

Canfield, S.M., et al., "The binding affinity of human IgG for its high affinity Fc receptor is determined by multiple amino acids in the C\subH\nor2 domain and is modulated by the hinge region" *Journal of Experimental Medicine*, 1991, 173(6), 1483-1491.

Capon, D.J., et al., "Designing CD4 Immunoadhesins for AIDS Therapy" *Nature*, 1989, 337, 525-531.

Chappel, M.S., et al., "Identification of Secondary FcγRI Binding Site within a Genetically Engineered Human IgG Antibody" *Journal of Biological Chemistry*, 1993, 268, 25124-25131.

Chappel, M.S., et al., "Identification of the Fcγ receptor class I binding site in human IgG through the use of recombinant IgG1/IgG2 hybrid and point-mutated antibodies" *Proc. Natl. Acad. Sci. USA*, 1991, 88(20), 9036-9040.

Clynes, R., et al., "Cytotoxic antibodies trigger inflammation through Fc receptors" *Immunity*, 1995, 3(1), 21-26.

Clynes, R., et al., "Fc receptors are required in passive and active immunity to melanoma" *Proc. Natl. Acad. Sci. USA*, 1998, 95(2), 652-656.

Clynes, R., et al., "Modulation of immune complex-induced inflammation in vivo by the coordinate expression of activation and inhibitory Fc receptors" *Journal of Experimental Medicine*, 1999, 189(1), 179-185.

Clynes, R., et al., "Uncoupling of immune complex formation and kidney damage in autoimmune glomerulonephritis" *Science*, 1998, 279(5353), 1052-1054.

Cosimi, A.B., "Clinical Development of Orthoclone OKT3" *Transplantation Proceedings*, 1987, (Suppl 1) XIX(2), 7-16.

Duncan, A.R., et al., "Localization of the binding site for the human high-affinity FC receptor on IgG" *Nature*, 1988, 332, 563-564.

Duncan, A.R., et al., "The binding site for Clq on IgG" *Nature*, 1988, 332, 738-740.

Gazzano-Santoro, H., et al., "A non-radioactive complement-dependent cytotoxicity assay for anti-CD20 monoclonal antibody" *Journal of Immunological Methods*, 1997, 202, 163-171.

Gergely, J., et al., "Fc receptors on lymphocytes and K cells" *Biochemical Society Transactions*, 1984, 12(5),739-743.

Ghebrehiwet, B., et al., "Isolation, cDNA cloning, and overexpression of a 33-kD cell surface glycoprotein that binds to the globular "heads" of C1q" *Journal of Experimental Medicine*, 1994, 179(6),1809-1821.

Ghetie, V., et al., "FcRn: the MHC class I-related receptor that is more than an IgG transporter" *Immunology Today*, 1997, 18(12), 592-598.

Ghetie, V., et al., "Abnormally short serum half-lives of IgG in/1422-microglobulin-deficient mice" *European Journal of Immunology*, 1996, 26(3), 690-696.

Ghetie, V., et al., "Increasing the serum persistence of an IgG fragment by random mutagenesis" *Nature Biotechnology*, 1997, 15(7), 637-640.

Gorman, C.M., et al., "Transient Production of Proteins Using an Adenovirus Transformed Cell Line" *DNA Prot. Eng. Tech.*, 1990, 2(1), 3-10.

Graham, F.L., et al., "Characteristics of a Human Cell Line Transformed by DNA from Human Adenovirus Type 5" *J. Gen. Virol.*, 1977, 36, 59-74.

Greenwood, J., et al., "Engineering multiple-domain forms of the therapeutic antibody CAMPATH-1H: effects of complement lysis" *Therapeutic Immunology*, 1994, 1(5), 247-255.

Greenwood, J., et al., "Structural motifs involved in human IgG antibody effector functions" *European Journal of Immunology*, 1993, 23(5), 1098-1104.

Guddat, L.W., et al., "Three-dimensional structure of a human immunoglobulin with a hinge deletion" *PNAS (USA)*, 1993, 90, 4271-4275.

Haagen, I., et al., "Interaction of Human Monocyte Fc\147 Receptors with Rat IgG2b: A New Indicator for the Fc\147RIIa (R-H131) Polymorphism" *J. Immunol.*, 1995, 154, 1852-1860.

Hadley, A.G., et al., "The functional activity of Fc\147RII and Fc\147RIII on subsets of human lymphocytes" *Immunology*, 1992, 76(3),446-451.

Harris, L.J., et al., "Crystallographic Structure of an Intact IgG1 Monoclonal Antibody" *Journal of Molecular Biology*, 1998, 275, 861-872.

Harris,L.J., et al., "Refined Structure of an Intact IgG2a Monoclonal Antibody" *Biochemistry*, 1997, 36, 1581-1597.

Hatta, Y., et al., "Association of Fc\147 receptor IIIB, but not of Fc\147 receptor IIA and IIIA, polymorphisms with systemic lupus erythematosus in Japanese" *Genes and Immunity*, 1999, 1, 53-60.

Heiken, H., et al., "T lymphocyte development in the absence of Fc\145 receptor I\147 subunit: analysis of thymic-dependent and independent \141\142 and \147\144 pathways" *European Journal of Immunology*, 1996, 26(8), 1935-1943.

Henry, A.J., et al., "Participation of the N-terminal region of C\1453 in the binding of human IgE to its high-affinity receptor F\145RI" *Biochemistry*, 1997, 36, 15568-15578.

Hogarth, P.M., et al., "Characterization of FcR Ig-binding sites and epitope mapping" *Immunomethods*, 1994, 4(1), 17-24.

Huizinga, T.W.J., et al, "Binding Characteristics of Dimeric IgG Subclass Complexes to Human Neutrophils" *Journal of Immunology*, 1989, 142, 2359-2364.

Hulett, M.D., et al., "Chimeric Fc Receptors Identify Functional Domains of the Murine High Affinity Receptors for IgG" *J. Immunol.*, 1991, 147, 1863-1868.

Jaakkola, K., et al., "In vivo detection of vascular adhesion protein-1 in experimental inflammation" *American Journal of Pathology*, 2000, 157(2), 463-471.

Janeway et al. Immunobiology, The Immune System in Health and Disease, *CB Ltd and Garland Publishing Inc.*, NY & London, 1994, 4 pages.

Jefferis, R., et al., "Molecular Definition of Interaction Sites on Human IgG for Fc Receptors (huFc\147R)" *Molecular Immunology*, 1990, 27(12), 1237-1240.

Kabat, E. et al. Sequences of Proteins of Immunological Interest, *5th edition*, Bethesda, MD:NIH, 1991, vol. 1, 669, 671, 687, 696.

Kim, J.K., et al., "Catabolism of the Murine IgG1 Molecule: Evidence That Both CH2-CH3 Domain Interfaces are Required for Persistence of IgG1 in the Circulation of Mice" *Scandinavian Journal Of Immunology*, 1994, 40(4), 457-465.

Kim, J.K., et al., "Identifying amino acid residues that influence plasma clearance of murine IgG1 fragments by site-directed mutagenesis" *European Journal of Immunology*, 1994, 24, 542-548.

Kim, J.K., et al., "Inhibition of Vascular Endothelial Growth Factor-Induced Angiogenesis Suppresses Tumour Growth in vivo" *Nature*, 1993, 362, 841-844.

Kim, J.K., et al., "Localization of the site of the murine IgG1 molecule that is involved in binding to the murine intestinal Fc receptor" *European Journal of Immunology*, 1994, 24, 2429-2434.

Kim, K.J., et al., "The Vascular Endothelial Growth Factor Proteins: Identification of Biologically Relevant Regions by Neutralizing Monoclonal Antibodies" *Growth Factors*, 1992, 7(1), 53-64.

Koene, H.R., et al., "FcγRIIIa-158V/F Polymorphism Influences the Binding of the IgG by Natural Killer Cell Fc\147RIIIa, Independently of the Fc\147RIIIa-48L/R/H Phenotype" *Blood*, 1997, 90(3),1109-1114.

Kunkel, T.A., "Rapid and Efficient Site-Specific Mutagenesis Without Phenotypic Selection" *Proc. Natl. Acad. Sci.*, 1985, 82, 488-492.

Lauvrak, V., et al., "Identification and characterisation of C1q-binding phage displayed peptides" *Biological Chemistry*, 1997, 378(12), 1509-1519.

Lehrnbecher, T., et al., "Variant genotypes of Fc\147RIIIA influence the development of Kaposi's sarcoma in HIV-infected men" *Blood*, 2000, 95(7), 2386-2390.

Lehrnbecher, T., et al., "Variant genotypes of the low-affinity Fc\147 receptors in two control populations and a review of low-affinity Fc\147 receptors polymorphisms in control and disease populations" *Blood*, 1999, 94(12), 4220-4232.

Li, M., et al., "Reconstitution of human Fc\147RIII cell type specificity in transgenic mice" *Journal of Experimental Medicine*, 1996, 183(3), 1259-1263.

Lifely, M.R., et al., "Glycosylation and biological activity of CAMPATH-1H expressed in different cell lines and grown under different culture conditions" *Glycobiology*, 1995, 5(8), 813-822.

Lorenz, A., "Strong association between the responder status of the FcγII receptor and recurrent spontaneous abortion," *Europ. J. Immunogenetics*, 1995, 22, 397-401.

Lucas, B.K., et al., "High-level production of recombinant proteins in CHO cells using a dicistronic DHFR intron expression vector" *Nucleic Acids Research*, 1996, 24(9), 1774-1779.

Lund, J., et al., "Human Fc\147\norRI and Fc\147\nor RII interact with distinct but overlapping sites on human IgG" *Journal of Immunology*, 1991, 147(8), 2657-2662.

Lund, J., et al., "Multiple binding sites on the C/subH/nor2 domain of IgG for mouse Fc\147\norR11" *Molecular Immunology*, 1992, 29(1), 53-59.

Lund,J. et al., "Multiple Interactions of the IgG with Its Core Oligosaccharide Can Modulate Recognition by Complement and Human Fc\147 Receptor I and Influence the Synthesis of Its Oligosaccharide Chains" *J. Immunol.*, 1996, 157, 4963-4969.

Lund, J., et al., "Oligosaccharide-protein interactions in IgG can modulate recognition by Fc\147 receptors" *FASEB Journal*, 1995, 9, 115-119.

Medesan, C., et al., "Comparative studies of rat IgG to further delineate the Fc: FcRN interaction site" *European Journal of Immunology*, 1998, 28, 2092-2100.

Medesan, C., et al., "Delineation of the amino acid residues involved in transcytosis and catabolism of mouse IgG1" *Journal of Immunology*, 1997, 158(5), 2211-2217.

Medesan, C., et al., "Localization of the site of the IgG molecule that regulates maternofetal transmission in mice" *European Journal of Immunology*, 1996, 26(10), 2533-2536.

Meng, Y.G., et al., "Green fluorescent protein as a second selectable markerfor selection for high producing clones from transfected CHO cells" *Gene*, 2000, 242, 201-207.

Miller, K.L., et al., "A Novel Role for the Fc Receptor\147 Subunit: Enhancement of the Fc\147R Ligand Affinity" *Journal of Experimental Medicine*, 1996, 183, 2227-2233.

Morgan, A., et al., "The N-terminal end of the C\subH\nor2 domain of chimeric human IgG1 anti-HLA-DR is necessary for C1q, Fc\147\norRI and Fc\147\norRIII binding" *Immunology*, 1995, 86(2), 319-324.

Morrison, S.L. et al., "Structural Determinants of Human IgG Function" *Immunologist*, 1994, 2, 119-124.

Nagarajan, S., et al., "Ligand binding and phagocytosis by CD16 (Fc\147\nor receptor III) isoforms. Phagocytic signalling by associated \172\nor and \147\nor subunits in Chinese hamster ovary cells" *Journal of Biological Chemistry*, 1995, 270(43), 25762-25770.

Ngo, J.T., et al., "Computational Complexity, Protein Structure Prediction, and the Levinthal Paradox" *The Protein Folding Problem and Tertiary Structure Prediction*, Merz & Le Grand, Boston:Birkhauser, 1994, 491-495.

Nieto, A., et al., "Involvement of the Fc\147 receptor IIIA genotypes in susceptibility to rheumatoid arthritis" *Arthritis and Rheumatism*, 2000, 43(4), 735-739.

Okada, H., et al., "Cutting Edge: Role of the inositol phosphatase SHIP in B cell receptor-induced Ca\sup2+\nor oscillatory response" *Journal of Immunology*, 1998, 161(10), 5129-5132.

Papac, D.I., et al., "A high-throughput microscale method to release N-linked oligosaccharide from glycoproteins for matrix-assisted laser desorption/ionization time-of-flight mass spectrometric analysis" *Glycobiology*, 1998, 8(5), 445-454.

Papac, D.I., et al., "Analysis of Acidic Oligosaccharides and Glycopeptides by Matrix-Assisted Laser Desorption/Ionization Time-of-Flight Mass Spectrometry" *Anal. Chem.*, 1996, 68, 3215-3223.

Popov, S., et al., "The stoichiometry and affinity of the interaction of murine Fc fragments with the MHC class I-related receptor, FcRn" *Molecular Immunology*, 1996 33(6), 521-530.

Porges, A.J., et al., "Novel Fc\147 Receptor I Family Gene Products in Human Mononuclear Cells" *J. Clin. Invest.*, 1992, 90, 2102-2109.

Presta, L.G., et al., "Humanization of an Anti-Vascular Endothelial Growth Factor Monoclonal Antibody for the Therapy of Solid Tumors and Other Disorders" *Cancer Research*, 1997, 57(20), 4593-4599.

Raghavan, M., et al., "Fc Receptors and their Interactions with Immunoglobulins" *Annu. Rev. Cell. Dev. Biol.*, 1996, 12, 181-220.

Raghavan, M., et al., "Analysis of the pH dependence of the neonatal Fc receptor/immunoglobulin G interaction using antibody and receptor variants" *Biochemistry*, 1995, 34(45), 14649-14657.

Ravetch, J.V., et al., "Divergent roles for Fc receptors and complement in vivo" *Annual Review of Immunology*, 1998, 16, 421-432.

Ravetch, J.V., "Fc receptors" *Current Opinion in Immunology*, 1997, 9(1):121-125.

Ravetch, J.V., "Fc receptors: rubor redux" *Cell*, 1994, 78(4), 553-560.

Reff, M.E., et al., "Depletion of B cells in vivo by a chimeric mouse human monoclonal antibody to CD20" *Blood*, 1994, 83(2), 435-445.

Sarmay, G., et al., "Ligand inhibition studies on the role of Fc receptors in antibody-dependent cell-mediated cytotoxicity" *Molecular Immunology*, 1984, 21(1), 43-51.

Sarmay, G., et al., "Mapping and comparison of the interaction sites on the Fc region of IgG responsible for triggering antibody dependent cellular cytotoxicity (ADCC) through different types of human Fc\147\nor receptor" *Molecular Immunology*, 1992, 29(5), 633-639.

Sensel, M.G., et al., "Amino acid differences in the N-terminus of C\subH\nor2 influence the relative abilities of IgG2 and IgG3 to activate complement" *Molecular Immunology*, 1997, 34(14),1019-1029.

Shores, E.W., et al., "T cell development in mice lacking all T cell receptor \172 family members (\172,\150, and Fc\145RI\147)" *Journal of Experimental Medicine*, 1998, 187(7), 1093-1101.

Sondermann, P., et al., "Crystal structure of the soluble form of the human Fc\147-receptor IIb: a new member of the immunoglobulin superfamily at 1.7 A resolution" *EMBO Journal*, 1999, 18(5), 1095-1103.

Sondermann, P., et al., "The 32-A crystal structure of the human IgG1 Fc Fragment-Fc\147RIII complex" *Nature*, 2000, 406, 267-273.

Strohmeier, G., et al., "Neutrophil functional responses depend on immune complex valency" *Journal of Leukocyte Biology*, 1995, 58(4), 403-414.

Strohmeier, G.R., et al., "Role of the Fc\147\norR subclasses Fc\147\norRII and Fc\147\norRIII in the activation of human neutrophils by low and high valency immune complexes" *Journal of Leukocyte Biology* ,1995, 58(4), 415-422.

Suzuki, Y., et al., "Distinct contribution of Fc receptors and angiotensin II-dependent pathways in anti-GBM glomerulonephritis" *Kidney International*, 1998, 54(4), 1166-1174.

Sylvestre,D.L., et al., "A dominant role for mast cell Fc receptors in the Arthus reaction" *Immunity*, 1996, 5(4), 387-390.

Sylvestre, D.L., , "Fc receptors initiate the Arthus reaction: redefining the inflammatory cascade" *Science*, 1994, 265(5175), 1095-1098.

Sylvestre, D., et al., "Immunoglobulin G-mediated inflammatory responses develop normally in complement-deficient mice" *Journal of Experimental Medicine*, 1996, 184(6), 2385-2392.

Tamm, A., et al., "The IgG binding site of human Fc\147\norRIIIB receptor involves CC' FG loops of the membrane-proximal domain" *Journal of Biological Chemistry*, 1996, 271(7), 3659-3666.

Tao, M., et al., "Structural features of human immunoglobulin G that determine isotype-specific differences in complement activation" *Journal of Experimental Medicine*, 1993, 178(2), 661-667.

Tao, M., et al., "Studies of aglycosylated chimeric mouse-human IgG. Role of Carbohydrate in the Structure and Effector Functions Mediated by the Human IgG Constant Region" *Journal of Immunology*, 1989, 143(8), 2595-2601.

Tao, M., et al., "The differential ability of human IgG1 and IgG4 to activate complement is determined by the COOH-terminal sequence of the C\subH\nor2 domain" *Journal of Experimental Medicine*, 1991, 173(4),1025-1028.

Tax, W.J.M., et al., "Fc receptors for mouse IgG1 on human monocytes: polymorphism and role in antibody-induced T cell proliferation," *Journal of Immunology*, 1984, 133(3), 1185-1189.

Ting, A.T., et al., "Fc\147 receptor activation induces the tyrosine phosphorylation of both phospholipase C (PLC)-\1471 and PLC-\1472 in natural killer cells" *Journal of Experimental Medicine* 1992, 176(6), 1751-1755.

Umana, P., et al., "Engineered glycoforms of an antineuroblastoma IgG1 with optimized antibody-dependent cellular cytotoxic activity" *Nature Biotechnology*, 1999, 17, 176-180.

Urfer, R., et al., "High resolution mapping of the binding site of TrkA for nerve growth factor and TrkC for neurotrophin-3 on the second immunoglobulin-like domain of the Trk receptors" *Journal of Biological Chemistry*, 1998, 273(10), 5829-5840.

Van de Winkel, J.G.J., et al., "Biology of human immunoglobulin G Fc receptors" *Journal of Leukocyte Biology*, 1991, 49(5), 511-524.

Vance, B.A., et al., "Binding of monomeric human IgG defines an expression polymorphism of Fc\147RIII on large granular lymphocyte/natural killer cells" *Journal of Immunology*, 1993, 151(11), 6429-6439.

Warmerdam, P.A.M., et al., "A single amino acid in the second Ig-like domain of the human Fc\147\nor receptor II is critical for human IgG2 binding" *Journal of Immunology*, 1991, 147(4), 1338-1343.

Weng, Z., et al., "Computational determination of the structure of rat Fc bound to the neonatal Fc receptor" *Journal of Molecular Biology*, 1998, 282(2), 217-225.

Werther, W.A., et al., "Humanization of an Anti-Lymphocyte Function-Associated Antigen (LFA)-1 Monoclonal Antibody and Reengineering of the Humanized Antibody for Binding to Rhesus LFA-1" *J. of Immunology*, 1996, 157, 4986-4995.

Woof, J.M., et al., "Localisation of the monocyte-binding region on human immunoglobulin G" *Molecular Immunology*, 1986, 23(3), 319-330.

Wright, A., et al.,, "Effect of altered C\subH\nor2-associated carbohydrate structure on the functional properties and in vivo fate of chimeric mouse-human immunoglobulin G1" *Journal of Experimental Medicine*, 1994, 180(3), 1087-1096.

Wu, J., et al., "A novel polymorphism of Fc\147RIIIA (CD16) alters receptor function and predisposes to autoimmune disease" *Journal of Clinical Investigation*, 1997, 100(5), 1059-1070.

Xu, Y., et al., "The N-terminal sequence of the C\subH\nor2 domain controls the differential ability of human IgG1 and IgG2 to activate complement" *Journal of Immunology*, 1993, (abstract No. 862), 150(8), 152A.

Yap S., et al., "Human Fc gamma receptor IIA (Fc\147RIIA) genotyping and association with systemic lupus erythematosus (SLE) in Chinese and Malays in Malaysia" *Lupus*, 1999, 8(4), 305-310.

U.S. Appl. No. 09/483,588, filed Jan. 14, 2000, Presta.

U.S. Appl. No. 09/713,425, filed Nov. 15, 2000, Presta.

Clynes et al., "Inhibitory Fc Receptors Modulate In Vivo Cytotoxicity Against Tumor Targets," *Nature Medicine*, vol. 6, No. 4, 2000, pp. 1078-8956.

D'Ambrosio et al., "The Ship Phosphate 1-15 Becomes Associated With FcgammaRIIB1 And Is Tyrosine Phosphorylated During Negative Signaling," *Immunology Letters*, 1996, vol. 54, No. 2-3, pp. 77-82.

Liu et al., "Protein Tyrosine Phosphorylation Triggered By Human Fcgamma-RII," *Biochemical And Biophysical Research Communications*, vol. 201, No. 2, pp. 829-834.

Muraille et al., "The SH2 Domain Containing Inositol 5-Phosphatase SHIP2 Associates To The Immunoreceptor Tyrosine-Based Inhibition Motif Of FcgammaRIIB in B Cells Under Negative Signaling," *Immunology Letters*, 2000, vol. 72, No. 1, pp. 7-15.

Houghton AN and Scheinberg DA, "Monoclonal Antibody Therapies—a 'Constant' Threat to Cancer", Nature Medicine, vol. 6, No. 4, Apr. 2000, pp. 373-374.

\* cited by examiner

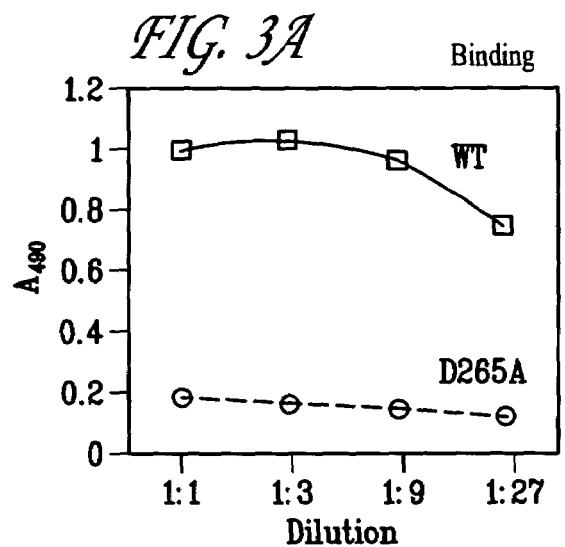
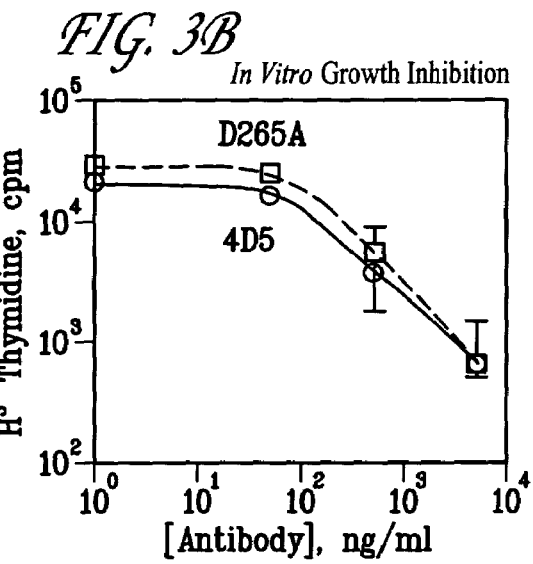
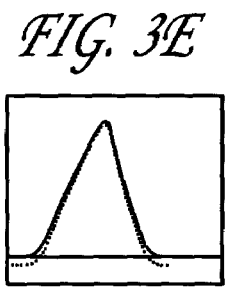
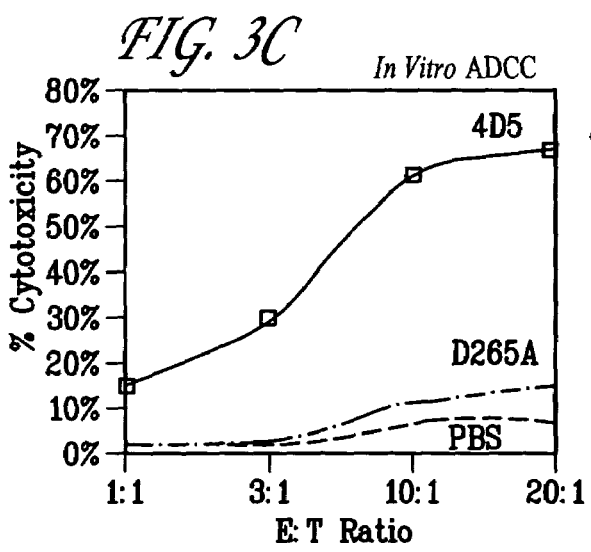
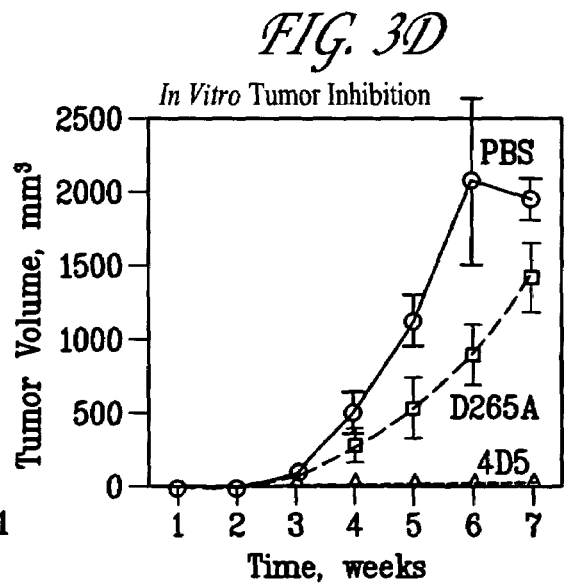

ENHANCEMENT OF ANTIBODY-MEDIATED IMMUNE RESPONSES

CROSS-REFERENCE TO RELATED APPLICATIONS

This application claims priority to U.S. Provisional Patent Applications, Ser. No. 60/198,550, filed Apr. 13, 2000, and Ser. No. 60/204,254, filed May, 15, 2000, each of which is incorporated herein by reference.

STATEMENT REGARDING FEDERALLY SPONSORED RESEARCH

The research leading to the present invention was supported in part, by National Institutes of Health Grant No. CA 80757. Accordingly, the U.S. Government may have certain rights in this invention.

FIELD OF THE INVENTION

The present invention relates to enhancing the function of anti-tumor antibodies by regulating FcγR activity.

BACKGROUND OF THE INVENTION

The interaction of antibodies and antibody-antigen complexes with cells of the immune system effects a variety of responses, including antibody-dependent cell-mediated cytotoxicity (ADCC) and complement-dependent cytotoxicity (CDC), phagocytosis, inflammatory mediator release, clearance of antigen, and antibody half-life (reviewed in Daëron, Annu. Rev. Immunol., 1997; 15:203-234; Ward and Ghetie, Therapeutic Immunol., 1995; 2:77-94; Ravetch and Kinet, Annu. Rev. Immunol., 1991; 9:457-492, each of which is incorporated herein by reference).

Antibody constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, and IgG4; IgA1 and IgA2. The heavy chain constant regions that correspond to the different classes of immunoglobulins are called α, δ, ε, γ, and μ, respectively. Of the various human immunoglobulin classes, human IgG1 and IgG3 mediate ADCC more effectively than IgG2 and IgG4.

Papain digestion of antibodies produces two identical antigen binding fragments, called Fab fragments, each with a single antigen binding site, and a residual "Fc" fragment, whose name reflects its ability to crystallize readily. The Fc region is central to the effector functions of antibodies. The crystal structure of the human IgG Fc region has been determined (Deisenhofer, Biochemistry, 20:2361-2370 (1981), which is incorporated herein by reference). In human IgG molecules, the Fc region is generated by papain cleavage N-terminal to Cys 226.

The effector functions mediated by the antibody Fc region can be divided into two categories: (1) effector functions that operate after the binding of antibody to an antigen; these functions involve the participation of the complement cascade or Fc receptor (FcR)-bearing cells; and (2) effector functions that operate independently of antigen binding; these functions confer persistence in the circulation and the ability to be transferred across cellular barriers by transcytosis (Ward and Ghetie, Therapeutic Immunology, 1995, 2:77-94, which is incorporated herein by reference).

While binding of an antibody to the requisite antigen has a neutralizing effect that might prevent the binding of a foreign antigen to its endogenous target (e.g., receptor or ligand), efficient effector functions are also required for removing and/or destroying foreign antigens.

Several antibody effector functions are mediated by Fc receptors (FcRs), which bind the Fc region of an antibody. FcRs are defined by their specificity for immunoglobulin isotypes: Fc receptors for IgG antibodies are referred to as FcγR, for IgE as FcεR, for IgA as FcαR and so on. Surface receptors for immunoglobulin G are present in two distinct classes—those that activate cells upon their crosslinking ("activation FcRs") and those that inhibit activation upon co-engagement ("inhibitory FcRs"). Activation FcRs for IgG require the presence of the Immune Tyrosine Activation Motif (ITAM) to mediate cellular activation. This 19 amino acid sequence, found in the cytoplasmic tail of the receptors or their associated subunits, interacts with src and syk families of tyrosine kinases sequentially. Upon crosslinking of an activation FcγR by an immune complex, ITAM sequences trigger the activation of these tyrosine kinases, which in turn activate a variety of cellular mediators, like PI3K, PLCγ and Tec kinases. The net result of these activation steps is to increase intracellular calcium release from the endoplasmic reticulum stores and opening of the capacitance coupled calcium channel to generate a sustained calcium response. These calcium fluxes are critical for the exocytosis of granular contents, stimulation of phagocytosis and ADCC responses and activation of specific nuclear transcription factors. Opposing these activation responses is the inhibitory FcγR. Inhibitory signaling is dependent on a 13 amino acid cytoplasmic sequence called the Immune Tyrosine Inhibitory Motif (ITIM). Upon co-ligation of an ITAM containing receptor to the inhibitory FcγR, a critical tyrosine residue in the ITIM becomes phosphorylated, leading to the recruitment of a specific SH2-containing inositol polyphosphate 5 phosphatase called SHIP. SHIP catalyzes the hydrolysis of the membrane inositol lipid, PIP3, thereby preventing activation of PLCγ and Tec kinases and abrogating the sustained calcium flux mediated by the influx of calcium through the capacitance coupled channel.

Three subclasses of FcγR have been identified: FcγRI (CD64), FcγRII (CD32) and FcγRIII (CD16). Because each FcγR subclass is encoded by two or three genes, and alternative RNA splicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22.

The mouse expresses two activation FcγRs, FcRI and FcRIII, oligomeric surface receptors with a ligand binding α subunit and an ITAM containing γ subunit. The inhibitory receptor is FcγRIIB, a single chain receptor with an ITIM sequence found in the cytoplasmic tail of the ligand binding α chain. FcRIIB and FcRIII bind monomeric IgG with an affinity constant of $1 \times 10^6$; hence, under physiological conditions they do not bind monomeric IgG, but interact with multimeric IgG immune complexes with low affinity and high avidity. FcRIII is the physiologically important activation FcR for mediating inflammatory disease triggered by cytotoxic antibodies or pathogenic immune complexes. FcRIII is expressed on NK cells, macrophages, mast cells and neutrophils in the mouse. It is not found on B cells, T cells or circulating monocytes. FcRIIB is found on B cells, macrophages, mast cells, neutrophils. It is not found on T cells or NK cells. FcRII and III have greater than 90% sequence identity in their extracellular, ligand binding domain.

The situation in the human is more complex. There are two low-affinity activation FcRs for IgG—FcγRIIA and FcγRIIIA. FcγRIIA is a single-chain low affinity receptor for IgG, with an ITAM sequence located in its cytoplasmic tail. It is expressed on macrophages, mast cells, monocytes, neutrophils and some B cells. It is 90% homologous in its extracellular domain to the human inhibitory FcRIIB molecule, which has an ITIM sequence in its cytoplasmic domain, expressed on B cells, macrophages, mast cells, neutrophils, monocytes but not NK cells or T cells. FcRIIIA is an oligomeric activation receptor consisting of a ligand binding α subunit and an ITAM containing γ or ζ subunit. It is expressed on NK cells, macrophages and mast cells. It is not expressed on neutrophils, B cells or T cells. In addition, a receptor with greater than 95% sequence identity in its extracellular domain called FcRIIIB is found on human neutrophils as a GPI-anchored protein. It is capable of binding immune complexes but not activating cells in the absence of association with an ITAM containing receptor like FcRIIA. FcRII and FcRIII are about 70% identical in their ligand binding extracellular domains.

Thus, in the human, IgG cytotoxic antibodies interact with four distinct low-affinity receptors—two of which are capable of activating cellular responses, FcRIIA and FcRIIIA, one of which is inhibitory, FcRIIB and one of which will bind IgG complexes but not trigger cellular responses, FcRIIIB. Macrophages express FcRIIA, FcRIIB and FcRIIIA, neutrophils express FcRIIA, FcRIIB and FcRIIIB, while NK cells express only FcRIIIA. The efficacy of a therapeutic anti-tumor antibody will thus depend on the specific interactions with activation, inhibition and inert low-affinity FcRs, differentially expressed on distinct cell types.

Well-defined tumor models for which therapeutic anti-tumor antibodies have been developed are known. For example, antibodies directed against the HER2/neu growth factor receptor prevent the growth of breast carcinoma cells in vitro and in vivo. Similarly, antibodies directed to the CD20 antigen on B cells arrests the growth of non-Hodgkin's lymphoma (Taji, H. et al., Jpn. J. Cancer Res., 1998, 89:748, which is incorporated herein by reference). These antibodies were developed based on their ability to interfere with tumor cell growth in vitro and are representative of a class which include those with specificities for the EGF receptor (Masul, H. et al., J. Cancer Res., 1986, 46:5592, which is incorporated herein by reference), IL-2R (Waldmann, T. A., Ann. Oncol., 1994, 5 Supp. 1:13-7, which is incorporated herein by reference) and others (Tutt, A. L. et al., J. Immunol., 1998, 161: 3176, which is incorporated herein by reference). HERCEPTIN®, a humanized antibody specific for the cellular proto-oncogene p185HER-2/neu (Pegram, M. D. et al., J. Clin. Oncol. 1998, 16:2659; Carter, P. et al., Proc. Natl. Acad. Sci. USA, 1992, 89:4285-4289, each of which is incorporated herein by reference), and RITUXAN®, a chimeric antibody specific for the B cell marker CD20 (Leget, G. A. and Czuczman, M. S., Curr. Opin. Oncol., 1998, 10:548-51, which is incorporated herein by reference), are approved for the treatment of HER-2 positive breast cancer and B cell lymphoma, respectively. A number of in vitro studies indicated that the critical mechanism responsible for the anti-tumor activities of HERCEPTIN® and its mouse parent molecule 4D5 are due to receptor-ligand blockade (Kopreski, M. et al., Anticancer Res., 1996, 16:433-6; Lewis, G. D. et al., Cancer Immunol. Immunother., 1993, 37:255-63, each of which is incorporated herein by reference), while other in vitro studies have suggested that activities such as antibody dependent cellular cytotoxicity (ADCC) may be of importance (Carter, 1992, supra; Lewis, G. D. et al., Cancer Immunol. Immunother., 1993, 37:255-63, which is incorporated herein by reference). In vitro studies with RITUXAN® and its murine parent 2B8 have suggested a direct pro-apoptotic activity may be associated with this antibody (Shan, D. et al., Blood, 1998, 91:1644-52, which is incorporated herein by reference).

Thus, multiple mechanisms have been proposed for the ability of anti-tumor antibodies to mediate their effects in vivo, including extended half-life, blockade of signaling pathways, activation of apoptosis and effector cell mediated cytotoxicity. The elucidation of a mechanism that enhances the ability of anti-tumor antibodies to effectively treat tumors is highly desirable.

SUMMARY OF THE INVENTION

The present invention represents an important improvement over prior art efforts to regulate antibody-mediated immune responses by recognizing the key role played by FcγRIIB in modulating antibody-mediated cytotoxicity. Thus the invention advantageously provides a method for enhancing cytotoxicity elicited by a therapeutic antibody in vivo in a human. The method of the invention comprises disrupting activation of SHIP by Fc-gamma-receptor IIB (FcγRIIB). Preferably, antibody binding is inhibited by modifying the Fc portion of the antibody to reduce its affinity for FcγRIIB. The invention is particularly useful to enhance the activity and thus effectiveness of anti-tumor antibodies.

The invention also provides an antibody with a variant Fc region, which antibody binds FcγRIIB with reduced affinity. Preferably, the antibody binds activating Fc-receptors with at least the same affinity as wildtype antibody. As noted above, these characteristics are particularly useful for an anti-tumor antibody.

These and other aspect of the invention will be better understood by reference to the Drawings, Detailed Description, and Examples.

DESCRIPTION OF THE DRAWINGS

FIGS. 3A, 3B, 3C, 3D, and 3E show in vitro and in vivo properties of D265A mutant antibody. FIG. 3A—FcγRIII binding. Both wildtype and mutant Fc fragments were grafted onto an antihuman IgE Fab fragment. Solid phase binding assays were performed with human IgE/antihuman IgE hexamenic complexes and recombinant FcγRIII coated plates. FIG. 3B—Growth inhibition of BT474MI cells. FIG.

3E—FACS analysis of BT474MI cells demonstrates equivalent avidities of 4D5 (solid line) and D265A (dotted line) for cell surface p185HER2/neu. $^3$H-thymidine incorporation of BT474M1 cells was measured in the presence of either 4D5 or D265A antibodies. FIG. 3C—NK cell ADCC of chromium-labeled tumor targets. Chromium labeled SKBR-3 cells were incubated with NK effector cells at varying ratios and release of label quantitated. FIG. 3D—In vivo growth of breast carcinoma cells: Athymic BALB/c nu/nu animals were implanted with BT474M1 xenografts and their growth measured as described in FIG. 1 in response to treatment with 4D5, D265A or PBS.

DETAILED DESCRIPTION

Figure 1A:
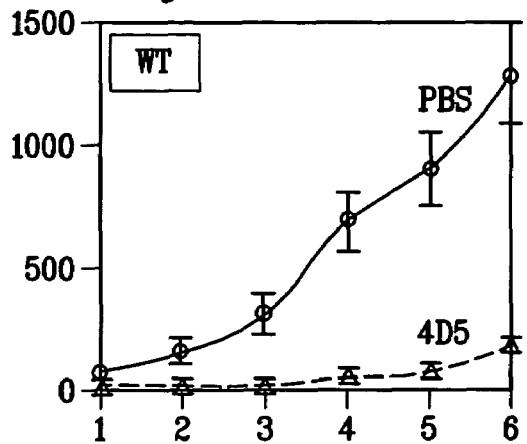
FIGS. 1A, 1B, 1C, 1D, 1E, and 1F show that anti-tumor activity of 4D5, HERCEPTIN®, and RITUXAN® require FcγR activating receptors. Nude mice (6-10 per group) were injected subcutaneously with $5 \times 10^6$ BT474M1 cells followed by weekly injections of mAb 4D5 (FIG. 1A and FIG. 1B) or HERCEPTIN® (FIGS. 1C and 1D) or RITUXAN® (FIGS. 1E and 1F). Antibody-dependent tumor protection observed in BALB/c nude mice (FIGS. 1A, 1C, and 1E) is absent in FcγRγ$^{-/-}$ nude mice (FIGS. 1B, 1D, and 1F). All experiments were repeated three times with similar results.
Figure 1B:
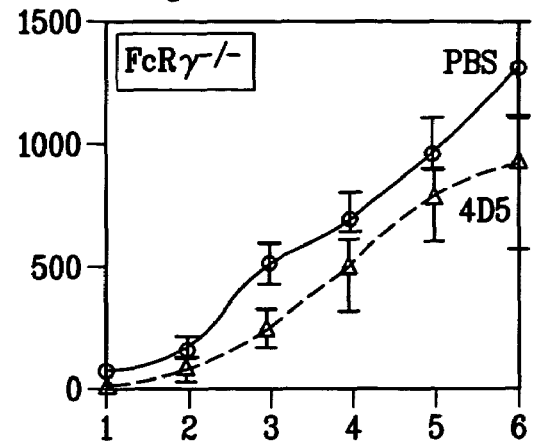
Figure 1C:
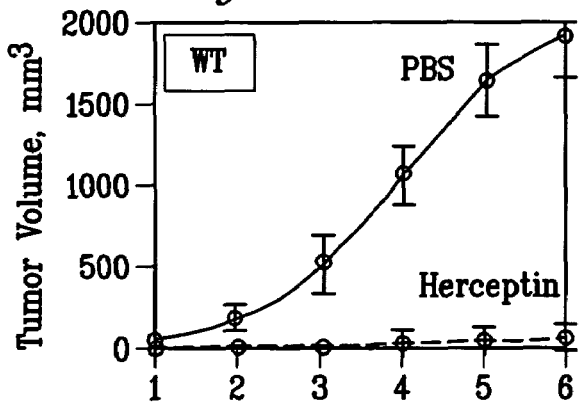
Figure 1D:
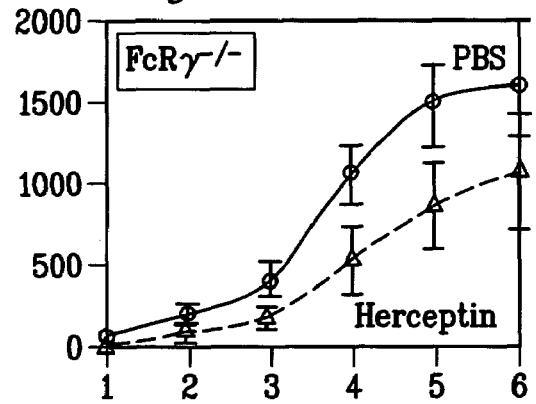

The present invention provides an advantageous strategy for enhancing effector function of therapeutic antibodies, particular anti-tumor, anti-viral, and anti-microbial (bacteria and unicellular parasites) antibodies, in humans. Enhancing cytotoxicity elicited by a therapeutic antibody in vivo in a human comprises disrupting activation of SHIP by Fc-gamma-receptor IIB (FcγRIIB or FcRIIB). In particular, by disrupting therapeutic antibody binding to the inhibitory Fc receptor FcRIIB while retaining or enhancing binding to FcRIIA and FcRIIIA, or by preventing FcRIIB from activating SHIP, the invention significantly improves antibody efficacy.

The present invention is based, in part, on recognition that inhibitory receptors modulate the in vivo cytotoxic response against tumor targets. Experiments using a variety of syngeneic and xenograft models demonstrated that the inhibitory FcγRIIB molecule is a potent regulator of cytotoxicity in vivo, modulating the activity of FcγRIII on effector cells. While multiple mechanisms have been proposed to account for the anti-tumor activities of therapeutic antibodies, engagement of FcγRs on effector cells is now demonstrated to be a significant component of the in vivo activity of anti-tumor antibodies.

Murine monoclonal antibodies as well as the humanized, clinically effective therapeutics HERCEPTIN® and RITUXAN® engage both activation and inhibitory antibody receptors on myeloid cells, thus modulating their cytotoxic potential. Mice deficient in FcγRIIB display greatly enhanced antibody-mediated cytotoxicity; conversely, mice deficient in activating Fc receptors as well as antibodies engineered to disrupt Fc binding to those receptors are unable to arrest tumor growth in vivo. These results demonstrate that FcR-dependent mechanisms significantly contribute to the action of cytotoxic anti-tumor antibodies and suggest that an optimal anti-tumor antibody for human therapy binds preferentially to activation FcRs and minimally to the inhibitory partner FcγRIIB.

These data substantiate the importance of inhibiting FcRIIB function to a greater degree than earlier work has done, because it demonstrates the effects in vivo by measuring the direct effects of antibody-mediated cytotoxicity on a valid therapeutic model (tumor cells in transgenic mice). The in vivo results reflect the effects of multiple receptor interactions of both the activation and inhibitory classes, i.e., FcRI, FcRIIB, and FcRIII, under physiological conditions. These results stand in contrast, therefore, to ADCC data, which measure in vitro antibody activity mediated by FcRIII engagement. Indeed, the in vivo data were critical to the discovery that FcRIIB makes a dominant contribution to antibody-mediated cytotoxicity, and that disrupting FcRIIB greatly improves cytotoxicity.

DEFINITIONS

Throughout the present specification and claims, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), which is expressly incorporated herein by reference. The "EU index as in Kabat" refers to the residue numbering of the human IgG1 EU antibody.

A "parent polypeptide" is a polypeptide comprising an amino acid sequence which lacks one or more of the Fc region modifications disclosed herein and which differs in effector function compared to a polypeptide variant as herein disclosed. The parent polypeptide may comprise a native sequence Fc region or an Fc region with pre-existing amino acid sequence modifications (such as additions, deletions and/or substitutions).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, Mol. Immunol., 1985, 22:161-206, which is incorporated herein by reference).

The "CH3 domain" comprises the stretch of residues C-terminal to a CH2 domain in an Fc region (i.e., from about amino acid residue 341 to about amino acid residue 447 of an IgG).

"Hinge region" is generally defined as stretching from Glu216 to Pro230 of human IgG1 (Burton, Mol. Immunol., 1985, supra). Hinge regions of other IgG isotypes may be aligned with the IgG1 sequence by placing the first and last cysteine residues forming inter-heavy chain S-S bonds in the same positions.

The "lower hinge region" of an Fc region is normally defined as the stretch of residues immediately C-terminal to the hinge region, i.e., residues 233 to 239 of the Fc region. Prior to the present invention, FcγR binding was generally attributed to amino acid residues in the lower hinge region of an IgG Fc region.

The term "binding domain" refers to the region of a polypeptide that binds to another molecule. In the case of an FcR, the binding domain can comprise a portion of a polypeptide chain thereof (e.g., the α chain thereof) which is responsible for binding an Fc region. One useful binding domain is the extracellular domain of an FcR chain.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (FAM) in its cytoplasmic domain. Inhibiting receptor FcγRIIB contains an immunoreceptor tyrosine-based inhibition motif (ITIM) in its cytoplasmic domain (see review in Daëron, Annu. Rev. Immunol., 1997, 15:203-234; FcRs are reviewed in Ravetch and Kinet, Annu. Rev. Immunol., 1991, 9:457-92; Capel et al., Immunomethods, 1994, 4:25-34; and de Haas et al., J. Lab. Clin. Med., 1995, 126:330-41, each of which is incorporated herein by reference).

"Antibody-dependent cell-mediated cytotoxicity" and "ADCC" refer to an in vitro cell-mediated reaction in which nonspecific cytotoxic cells that express FcRs (e.g., monocytic cells such as Natural Killer (NK) cells and macrophages) recognize bound antibody on a target cell and subsequently cause lysis of the target cell. In principle, any effector cell with an activating FcγR can be triggered to mediate ADCC. The primary cells for mediating ADCC, NK cells, express FcγRIII only, whereas monocytes, depending on their state of activation, localization, or differentiation, can express FcγRI, FcγRII, and FcγRIII. FcR expression on hematopoietic cells is summarized in Ravetch and Kinet, Annu. Rev. Immunol., 1991, 9:457-92, each of which is incorporated herein by reference.

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

Antibodies

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined for the purpose of the present invention, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler and Milstein, Nature, 1975, 256:495-497, which is incorporated herein by reference, or may be made by recombinant DNA methods (see, e.g., U.S. Pat. No. 30 4,816,567, which is incorporated herein by reference). The "monoclonal antibodies" may also be isolated from phage antibody libraries using the techniques described in Clackson et al., Nature, 1991, 352:624-628 and Marks et al., J. Mol. Biol., 1991, 222:581-597, for example, each of which is incorporated herein by reference.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., Proc. Natl. Acad. Sci. USA, 1984, 81:6851-6855; Neuberger et al., Nature, 1984, 312:604-608; Takeda et al., Nature, 1985, 314: 452-454; International Patent Application No. PCT/GB85/00392, each of which is incorporated herein by reference).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues.

Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody optionally also will comprise at least a portion of an immunoglobulin constant region (Fc), typically that of a human immunoglobulin. For further details, see Jones et al., Nature, 1986, 321:522-525; Riechmann et al., Nature, 1988, 332:323-329; Presta, Curr. Op. Struct. Biol., 1992, 2:593-596; U.S. Pat. No. 5,225,539, each of which is incorporated herein by reference.

Inhibition by a Competitive Inhibitor

The present invention contemplates administering an effective amount of a competitive inhibitor that binds specifically to FcRIIB, without activating it, and thus prevents binding by a tumor specific antibody. For example, binding of monomeric molecules to FcRIIB prevents crosslinking of the receptor, which is required for activation.

Various competitive inhibitors can be used in the practice of this invention, including but by no means limited to anti-FcRIIB antibodies (preferably Fv antibodies to preclude development of a cytotoxic response) and peptides corresponding to the FcRIIB-binding sequence of immunoglobulins.

Small molecular weight competitive inhibitors of the FcRIIB binding site are effective at preventing the binding of cytotoxic antibodies to the inhibitory Fc receptor. Other targets for preventing activation of the inhibitory receptor include the dominant signaling molecule, SHIP. SHIP, an inositol polyphosphate 5-phosphatase, is essential for the biological activity of FcRIIB (Ono et al., Nature, 1996, 383:263; Ono et al., Cell, 1997, 90:293; Bolland et al., Immunity, 1998, 8:509, each of which is incorporated herein by reference). Competitive inhibitors of the inositol phosphatase activity of SHIP will abrogate the inhibitory activity of FcRIIB and thereby amplify the effective cytotoxic activity of IgG antibodies. The competitive inhibitors can include antibodies as well as small molecular weight antagonists.

Antibodies with Modified FcRIIB Binding Site

In a preferred embodiment, antibody binding is inhibited by modifying the Fc portion of the antibody to reduce its affinity for FcγRIIB, thus creating an antibody variant. A number of references describe techniques for modifying Fc portions to modulate binding affinity for FcRs (see PCT Publication Nos. WO 99/58572, WO 99/51642, WO 98/23289, WO 89/07142, WO 88/07089; U.S. Pat. Nos. 5,834,597 and 5,624,821, each of which is incorporated herein by reference).

An antibody variant with "altered" FcR binding affinity is one which has diminished FcγRIIB binding activity and enhanced cytotoxicity compared to a parent polypeptide or to a polypeptide comprising a native sequence Fc region.

The antibody variant which "mediates antibody-mediated cytotoxicity in the presence of human effector cells more effectively" than a parent antibody is one which in vitro or in vivo is substantially more effective at mediating cytotoxicity, when the amounts of antibody preferred variant is from about 1.5-fold to about 100-fold, e.g., from about two-fold to about fifty-fold, more effective at mediating cytotoxicity than the parent, e.g., in one or more of the in vivo assays disclosed herein.

An "amino acid modification" refers to a change in the amino acid sequence of a predetermined amino acid sequence. Exemplary modifications include an amino acid substitution, insertion and/or deletion. The preferred amino acid modification herein is a substitution.

An "amino acid modification at" a specified position, e.g., of the Fc region, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al., Meth. Enzym., 1991, 202:301-336, which is incorporated herein by reference. To generate such non-naturally occurring amino acid residues, the procedures of Noren et al., Science, 1989, 244:182, which is incorporated herein by reference, and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g., insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

In a specific embodiment, a modified antibody variant of the invention has reduced affinity for FcRIIB, but unchanged, or even enhanced, affinity for the stimulatory FcRs, FcRI and FcRIII.

In general, generation of these modified Fc domains involves the expression of a library of mutagenized dimeric IgG Fc domains in a compatible host, such as a yeast or a mammalian cell, and the screening of these surface expressed Fc domains with specific Fc receptors by either solid-phase or solution binding. Modified Fc domains with reduced binding to FcRIIB are identified in this manner.

Inhibiting Expression of FcγRIIB or SHIP

As discussed above, one method for enhancing tumor-specific (or any) antibody-mediated cytotoxicity involves inhibiting the expression of either the inhibitory Fc receptor, FcγRIIB, or the molecule that mediates signal transduction by this receptor, SHIP. There are numerous techniques for inhibiting expression of a target protein, including antisense and intracellular antibodies. The nucleic acids encoding these targets, and the proteins themselves, are well known (Brooks et al., J. Exp. Med., 1989, 170:1369; Damein, Proc. Natl. Acad. Sci. USA 1996, 93:1689; Kavanaugh et al., Curr. Biol. 1996, 6:438, each of which is incorporated herein by reference).

An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234, each of which is incorporated herein by reference), or alternatively they can be prepared synthetically (e.g., U.S. Pat. No. 5,780,607, which is incorporated herein by reference). There are numerous examples of the use of antisense nucleic acids to suppress gene expression (see U.S. Pat. Nos. 5,773,231 and 5,576,208; Hanna et al., J. Vasc. Surg, 2000, 31:770-780; Han et al., Am. J. Physiol. Renal Physiol., 2000, 278:F628-F634; Prati et al., Biotechnol. Bioeng., 2000, 68:239-244; Yang et al., Clin. Cancer Res., 2000, 6:1024-30; Yang et al., Clin. Cancer Res., 2000, 6:773-81; Mack and Robitzki, Prog. Neurobiol., 2000, 60:602-28, each of which is incorporated herein by reference).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437, which is incorporated herein by reference, describes heteroaromatic olignucleoside linkages. Nitrogen linkers or groups containing nitrogen can also be used to prepare oligonucleotide mimics (U.S. Pat. No. 5,792,844 and No. 5,783,682, each of which is incorporated herein by reference). U.S. Pat. No. 5,637,684, which is incorporated herein by reference, describes phosphoramidate and phosphorothioamidate oligomeric compounds. Also envisioned are oligonucleotides having morpholino backbone structures (U.S. Pat. No. 5,034,506, which is incorporated herein by reference). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991, which is incorporated herein by reference). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$;$NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Intracellular antibodies are also effective at inhibiting protein expression or function. Intracellular antibodies are typically single chain Fv constructs (Bird, Science, 1988, 242: 423-426; Huston et al., Proc. Natl. Acad. Sci. USA, 1988, 85:5879-5883; Ward et al., Nature, 1989, 334:544-546; U.S. Pat. Nos. 5,476,786, 5,132,405, and 4,946,778; Huse et al., Science 246:1275-1281, 1989, each of which is incorporated herein by reference). A number of studies report on their effectiveness at inhibiting intracellular protein function (Richardson et al., Gene Ther., 1998, 5:635-44; Marasco et al., Hum. Gene Ther., 1998, 9:1627-42; Cochet et al., Cancer Res., 1998, 58:1170-6; Curiel, Adv. Pharmacol., 1997, 40:51-84, each of which is incorporated herein by reference).

Inhibiting Signal Transduction

In another embodiment, SHIP activation is inhibited by an inositol phosphatase inhibitor. The inositol polyphosphate 5-phosphatase activity of SHIP is both necessary and sufficient for transducing the inhibitory signal of FcRIIB (Ono et al., 1997, supra; Bolland et al., 1998, supra). It is uniquely associated with FcRIIB upon its phosphorylation by crosslinking to an ITAM-containing receptor, such as FcRIIA or FcRIIIA, as occurs in vivo when a cytotoxic antibody engages surface FcRs on macrophages, mast cells, neutrophils, or monocytes. Mutation of the phosphatase activity of SHIP inactivates FcRIIB, preventing inhibitory signaling and thereby acting to amplify the in vivo effect of cytotoxic antibody engagement of activation FcRs. While numerous classes of inositol phosphatases are known to exist, the 5-phosphatase activity of SHIP is distinctive, permitting the generation of SHIP-specific inhibitors. SHIP is expressed widely in hematopoeitic cells and is implicated in signaling from a variety of growth factor receptors, although the contribution of the phosphatase activity to those activities is not yet established. In any event, an inhibitor of SHIP phosphatase activity or recruitment to the phosphorylated FcRIIB ITIM motif will abrogate inhibitory signaling in the effected cell.

Recombinant Technology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. 1985); *Transcription And Translation* (B. D. Hames & S. J. Higgins, eds. 1984); *Animal Cell Culture* (R. I. Freshney, ed. 1986); *Immobilized Cells And Enzymes* (IRL Press, 1986); B. Perbal, *A Practical Guide To Molecular Cloning* (1984); F. M. Ausubel et al. (eds.), *Current Protocols in Molecular Biology*, John Wiley & Sons, Inc. (1994), each of which is incorporated herein by reference.

Molecular Biology—Definitions

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" or "operatively associated with" of transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (CLONTECH, Palo Alto, Calif.), pUC plasmids, pET plasmids (Novagen, Inc., Madison, Wis.), pRSET or pREP plasmids (Invitrogen, San Diego, Calif.), or pMAL plasmids (New England BioLabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995, which is incorporated herein by reference.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 1992, 7:980-990, which is incorporated herein by reference). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 1991, 2:320-330, which is incorporated herein by reference), defective herpes virus vector lacking a glyco-protein L gene (Patent Publication RD 371005 A, which is incorporated herein by reference), or other defective herpes virus vectors (International Patent Publication No. WO 94/21807, published Sep. 29, 1994; International Patent Publication No. WO 92/05263, published Apr. 2, 1994, each of which is incorporated herein by reference); an attenuated adenovirus vector, such as the vector described by Stratford-Perricaudet et al., J. Clin. Invest., 1992, 90:626-630, which is incorporated herein by reference; see also La Salle et al., Science, 1993, 259:988-990, which is incorporated herein by reference); and a defective adeno-associated virus vector (Samulski et al., J. Virol., 1987, 61:3096-3101; Samulski et al., J. Virol., 1989, 63:3822-3828; Lebkowski et al., Mol. Cell. Biol., 1988, 8:3988-3996, each of which is incorporated herein by reference).

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), CLONTECH (Palo Alto, Calif.; retroviral and baculoviral vectors), Genovo, Inc. (Sharon Hill, Pa.; adenoviral and AAV vectors), Genvec (Gaithersburg, Md.; adenoviral vectors), IntroGene (Leiden, Netherlands; adenoviral vectors), Molecular Medicine (retroviral, adenoviral, AAV, and herpes viral vectors), Norgen (Ontario, Canada; adenoviral vectors), Oxford BioMedica (Oxford, United Kingdom; lentiviral vectors), and Transgene (Strasbourg, France; adenoviral, vaccinia, retroviral, and lentiviral vectors).

Non-viral vectors can be introduced by lipofection, as naked DNA, or with other transfection facilitating agents (peptides, polymers, etc.). Synthetic cationic lipids can be used to prepare liposomes for transfection of a gene encoding a marker (Felgner, et al., Proc. Natl. Acad. Sci. U.S.A., 1987, 84:7413-7417; Felgner and Ringold, Science, 1989, 337:387-388; Mackey et al., Proc. Natl. Acad. Sci. U.S.A., 1988, 85:8027-8031; Ulmer et al., Science, 1993, 259:1745-1748, each of which is incorporated herein by reference). Useful lipid compounds and compositions for transfer of nucleic acids are described in International Patent Publications WO95/18863 and WO96/17823, and in U.S. Pat. No. 5,459,127, each of which is incorporated herein by reference. Lipids may be chemically coupled to other molecules for the purpose of targeting (see Mackey et al., supra). Targeted peptides, e.g., hormones or neurotransmitters, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO95/21931, which is incorporated herein by reference), peptides derived from DNA binding proteins (e.g., International Patent Publication WO96/25508, which is incorporated herein by reference), or a cationic polymer (e.g., International Patent Publication WO95/21931, which is incorporated herein by reference). It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem., 1992, 267:963-967; Wu and Wu, J. Biol. Chem., 1988, 263:14621-14624; Hartmut et al., Canadian Patent Application No. 2,012,311, filed Mar. 15, 1990; Williams et al., Proc. Natl. Acad. Sci. USA, 1991, 88:2726-2730, each of which is incorporated herein by reference). Receptor-mediated DNA delivery approaches can also be used (Curiel et al., Hum. Gene Ther., 1992, 3:147-154; Wu and Wu, J. Biol. Chem., 1987, 262:4429-4432, each of which is incorporated herein by reference). U.S. Pat. Nos. 5,580,859 and 5,589,466, each of which is incorporated herein by reference, disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci., 1998, 321:893; WO 99/01157; WO 99/01158; WO 99/01175, each of which is incorporated herein by reference).

The term "expression system" means a host cell and compatible vector under suitable conditions, e.g., for the expression of a protein coded for by foreign DNA carried by the vector and introduced to the host cell. Common expression systems include E. coli host cells and plasmid vectors, insect host cells and Baculovirus vectors, and mammalian host cells and vectors. In a specific embodiment, the protein of interest is expressed in COS-1 or $C_2C_{12}$ cells. Other suitable cells include CHO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed, e.g., a CHO cell.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}P$-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids encoding the protein. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Therapeutic Modulation of SHIP Activation by FcRIIB

The present invention provides strategies for enhancing antibody-based treatments (passive immunotherapy) of tumors, viruses, and microorganisms, i.e., conditions in which enhancement of immune response provides a therapeutic benefit.

The phrase "therapeutically effective" or "therapeutic" is used herein to mean to reduce by at least about 15 percent, preferably by at least 50 percent, more preferably by at least 90 percent, and most preferably eliminate, a clinically significant deficit in the activity, function and response of the subject. Alternatively, a therapeutically effective amount is sufficient to cause an improvement in a clinically significant condition in the subject. In accordance with the present invention, a therapeutic effect is achieved by inhibiting FcRIIB activity when a therapeutic antibody achieves greater effect than in the absence of FcRIIB inhibition. Such effects include improving cancer (by reducing tumor size, eliminating metastasises, increasing time to recurrence, or increasing survival); clearing an infection; quieting an acute infection; or eliminating parasites.

Therapeutic antibodies, and inhibitors of FcRIIB (collectively "therapeutic agents"), can be provided to subjects in pharmaceutically acceptable formulations. The phrase "pharmaceutically acceptable" refers to molecular entities and compositions that are physiologically tolerable and do not typically produce an allergic or similar untoward reaction when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, which is incorporated herein by reference.

According to the invention, the therapeutic agents can be formulated together or separately in a pharmaceutical composition of the invention to be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In another embodiment, the therapeutic agents can be delivered together or separately in a vesicle, in particular a liposome (see Langer, Science, 1990, 249:1527-1533; Treat et al., in *Liposomes in the Therapy of Infectious Disease and Cancer*, Lopez-Berestein and Fidler (eds.), Liss, New York, pp. 353-365 (1989); Lopez-Berestein, ibid, pp. 317-327; see generally ibid, each of which is incorporated herein by reference). To reduce its systemic side effects, this may be a preferred method for introducing the agents.

In yet another embodiment, the therapeutic agents can be delivered together or separately in a controlled release system. For example, a polypeptide may be administered using intravenous infusion with a continuous pump, in a polymer matrix such as poly-lactic/glutamic acid (PLGA), a pellet containing a mixture of cholesterol and the estrogen compound (SILASTICR™; Dow Corning, Midland, Mich.; see U.S. Pat. No. 5,554,601, which is incorporated herein by reference) implanted subcutaneously, an implantable osmotic pump, a transdermal patch, liposomes, or other modes of administration. In one embodiment, a pump may be used (see Langer, supra; Sefton, CRC Crit. Ref. Biomed. Eng., 1987, 14:201; Buchwald et al., Surgery, 1980, 88:507; Saudek et al., N. Engl. J. Med., 1989, 321:574, each of which is incorporated herein by reference). In another embodiment, polymeric materials can be used (see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, J., Macromol. Sci. Rev. Macromol. Chem., 1983, 23:61; Levy et al., Science, 1985, 228:190; During et al., Ann. Neurol., 1989, 25:351; Howard et al., J. Neurosurg., 1989, 71:105, each of which is incorporated herein by reference). In yet another embodiment, a controlled release system can be placed in proximity of the therapeutic target, e.g., a tumor or site of infection, thus requiring only a fraction of the systemic dose (see, e.g., Goodson, in *Medical Applications of Controlled Release*, supra, vol. 2, pp 115-138 (1984), which is incorporated herein by reference). Other controlled release systems are discussed in the review by Langer (Science, 1990, 249: 1527-1533), which is incorporated herein by reference.

A subject in whom administration of the antibody and FcRIIB-inhibitory agent provides an effective therapeutic regimen for a disease or disorder that benefits from enhanced immune activity, such as tumor therapy or treatment of an infectious microorganism or parasite, is preferably a human, but can be any animal, including a laboratory animal in the context of a clinical trial or screening or activity experiment. Thus, as can be readily appreciated by one of ordinary skill in the art, the methods and compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use. In a specific embodiment, the animal is a transgenic mouse that expresses human FcR chains.

Anti-Tumor Therapy

The present invention is directed the treatment of tumors, particularly solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas. The following are non-limiting preferred examples of the cancers treatable with the composition and methods of the present invention: melanoma, including stage-4 melanoma; ovarian, including advanced ovarian; leukemia, including but not limited to acute myelogenous leukemia; colon, including colon metastasized to liver; rectal, colorectal, breast, lung, kidney, and prostate cancers.

Anti-tumor antibodies can be generated against the tumor cells themselves, or against specific tumor cell antigens. There is substantial evidence that the same tumor antigens are expressed by different human melanoma tumors, suggesting that transformation-associated events may give rise to recurrent expression of the same tumor antigen in tumors of related tissue and/or cellular origin (Sahasrabudhe et al., J. Immunol., 1993, 151:6302-6310; Shamamian et al., Cancer Immunol. Immunother., 1994, 39:73-83; Cox et al., Science, 1994, 264:716; Peoples et al., J. Immunol., 1993, 151:5481-5491; Jerome et al., Cancer Res., 1991, 51:2908-2916; Morioke et al., J. Immunol., 1994, 153:5650-5658, each of which is incorporated herein by reference). Examples of such antigens include, but are not limited to, MART 1/MelanA, gp-100, and tyrosinase (melanoma); MAGE-1 and MAGE-3 (bladder, head and neck, non-small cell carcinoma); HPV E6 and E7 proteins (cervical cancer); HER2/neu/c-erbB-2 (breast cancer); HER3, HER4, Mucin (MUC-1) (breast, pancreas, colon, prostate); prostate specific antigen (PSA) (prostate); CD20 (B cell lymphoma); and CEA (colon, breast, GI).

Anti-Fungal, Anti-Viral, Anti-Bacterial, and Anti-Parasite Therapy

Anti-viral, anti-bacterial, and anti-parasite antibodies, with enhanced cytotoxic activity as a result of inhibition of FcRIIB, can be used to treat or clear infections by these microorganisms. Such viral infections include, but are by no means limited to, human immunodeficiency virus (HIV); hepatitis A virus, hepatitis B virus, hepatitis C virus, hepatitis D virus, and other hepatitis viruses; cytomagalovirus; herpes simplex virus; human papilloma viruses; Epstein-Barr virus; and other viral infections. Anti-viral antibodies are well known in the art, and supply a readily available reservoir of reagents for use with FcRIIB-inhibitory (including SHIP inhibitory) agents as set forth above, or can be modified as set forth above to have reduced FcRIIB binding affinity.

Examples of infectious bacteria that can be treated in accordance with the invention include, but are by no mean limited to, *S. pneumoniae, S. aureus, E. faecalis, E. coli, Salmonella, M leprae, M. tuberculosis, N. gonorrhoeae*, etc. Indeed, the present invention provides an avenue for enhancing the activity of antibodies generated against bacterial exported (surface) proteins, located in the bacterial coat or cell wall, e.g., as have been described for *S. pneumoniae* (U.S. Pat. No. 5,981,229, which is incorporated herein by reference).

The present invention also provides for enhancing the activity of cytotoxic antibodies generated to pathogenic fungi, such as *C. neoformans* and *C. albicans* (Yuan et al., J. Exp. Med., 1998, 187:641, which is incorporated herein by reference).

Examples of parasites that can be treated in accordance with the invention include, but are not limited to, trypanosomes, plasmodia (malaria microbe), shistosomes, etc. An important advantage of the present invention lies in the ability of the enhanced antibody-mediated cytotoxicity to clear the parasitic infection early, before the parasite can transform into a different stage or develop a new antigenic coat.

Pharmaceutical Kits

Another aspect of the present invention relates to pharmaceutical kits directed to enhancing the cytotoxicity of a therapeutic antibody by disrupting SHIP activation by FcγRIIB. In one embodiment a kit according to this aspect of the invention comprises a therapeutic antibody having reduced affinity for FcγRIIB, such as an antibody having a modified Fc domain. In another embodiment, the kit comprises a therapeutic antibody and a competitive inhibitor of FcγRIIB binding. In a further embodiment of the invention, the kit comprises a therapeutic antibody and an inhibitor of expression of FcγRIIB or SHIP, including, but not limited to, antisense nucleic acid molecules and intracellular antibodies. Optionally, the kit also includes instructions for use of the component antibodies and inhibitors, controls, and photos or figures depicting data.

The invention can be better understood by reference to the following Examples, which are provided by way of illustration and not by way of limitation.

EXAMPLES

Example 1

Inhibitory Fc Receptor Modulates In Vivo Cytotoxicity Against Tumor Targets

Materials and Methods

Melanoma metastasis model. Mice were injected intravenously with $1 \times 10^6$ B16 melanoma cells on day 0 and with either PBS or 20 µg of purified TA99 i.p. on days 0, 2, 4, 7, 9 and 11. A dose of 200 µg of mAb TA99 induced greater than 90% reduction in tumor metastasis in wild-type but not FcRγ$^{-/-}$ mice. However, at this lowered 20 µg dose TA99 only limited protection was provided against tumor metastasis in WT mice. Mice were sacrificed on day 14 and surface lung metastasis counted under a dissecting microscope.

Tumor xenograft models. For breast carcinoma xenograft experiments, $5 \times 10^6$ BT474M1 cells (BT474 subclone derived at Genentech, South San Francisco, Calif.) were injected subcutaneously on day 1 in 0.1 ml PBS mixed with 0.1 ml MATRIGEL (Collaborative Research, Bedford, Mass.). 2-4 month old BALB/c nude mice, γ$^{-/-}$ BALB/c nude mice or RII$^{-/-}$ BALB/c nude mice were injected subcutaneously with 17β-estradiol 60 day release pellets (0.75 mg/pellet) (Innovative Research of America, Sarasota, Fla.) 24 hrs prior to tumor cell injection. Therapeutic antibodies (obtained from vialed, clinical material, Genentech, Inc., South San Francisco, Calif.) were intravenously injected beginning on day 1 at 4 µg/mg loading dose, with weekly injections of 2 µg/mg for BALB/c nude and γ$^{-/-}$ BALB/c nude. A ten fold lower dose was used for the experiments shown in FIG. 3. For B cell lymphoma xenograft experiments, 2-4 month old BALB/c nude mice or γ$^{-/-}$ BALB/c nude mice were irradiated with 3.0 cGy prior to subcutaneous injection of $5 \times 10^6$ Raji B lymphoma cells. RITUXAN® was obtained from IDEC Pharmaceuticals, Inc. and given at a dose of 10 µg/gm weekly. Tumor measurements were obtained weekly.

Engineering of D265A mutant antibody and binding assays. Site-directed mutagenesis was performed using QUIKCHANGE Mutagenesis Kit (Stratagene, La Jolla, Calif.). Mutant antibody was transiently expressed in A293 cells in the pRK expression vector and conditioned supernatants were harvested and purified by protein G affinity column chromatography. The ability of various mutants to bind recombinant FcγRs was evaluated using an in vitro binding assay. Microtiter plates were coated with recombinant FcγRIII GST fusion protein at a concentration of 10 ng/well in PBS. Plates were washed with PBS, supplemented with 0.05% Tween-20 (wash buffer) then blocked for 1 hour at room temperature with 0.5% BSA, 50 mM TBS, 0.05% Tween-20, 2 mM EDTA pH 8.0 (ELISA buffer). The IgG1 Fc fragment of murine 4D5 as well as D265A was grafted onto the Fab of anti-human IgE (mAb E27) and recombinant antibody was produced as mentioned above. Addition of human IgE to antihuman E27 with wild type or mutant Fc domains in a 1:1 molar ratio in ELISA buffer led to the formation of homogeneous hexameric complexes. Complexes were added to the plates, washed five times in wash buffer and were detected by the addition of goat F(ab')$_2$ anti-mouse IgG, and subsequent colorimetric development.

Growth inhibition assays. BT474M1 cells were plated at $1 \times 10^4$, and allowed to adhere for 24 hours. Antibody was added at the indicated concentrations for 48 hours, followed by a 14 hour pulse with [H$^3$]thymidine. Cells were harvested, collected on filter mats, and counted in a WALLAC MICROBETA scintillation counter. BT474M1 cells were incubated with 4D5 or D265A antibody, and stained with FITC-conjugated goat anti-mouse IgG. Fluorescence intensity was measured on a FACSCAN flow cytometer.

In vitro ADCC assay. Adherent NK effector cells were obtained from IL-2 stimulated (250 U/ml, Sigma, St. Louis, Mo.) 14-day culture of nylon wool non-adherent splenocytes. 4-hour ADCC reactions were performed with $5 \times 10^4$ chromium-labeled HER2 overexpressing SK-BR3 breast carcinoma (ATCC, Manassas, Va.) target cells in 96-well plates in the presence or absence of antibody (10 µg/ml). Percentage (%) cytotoxicity was expressed as: counts in supernatant-spontaneous release (without effectors)/total counts incorporated-spontaneous release. Data are expressed as the mean of three replicate wells.

Results

Passive and active protection against pulmonary metastasis in the syngeneic B16 melanoma model has recently been demonstrated to require the presence of activation FcRs (2) on effector cells, such as NK cells. To determine whether the inhibitory FcγRIIB was a factor in determining the in vivo anti-tumor activity of mAb TA99 2, a protective IgG2a antibody specific for the melanoma differentiation antigen gp75 (TRP-1), C57B1/6 mice were crossed to an FcγRIIB deficient strain and then backcrossed to establish a syngeneic strain. Metastasis of B16 melanoma cells in the RIIB deficient background were identical to wild-type (almost total blackening of the lungs with metastatic melanoma tumor cells), demonstrating that the inhibitory receptor was not involved in tumor growth or spread. In contrast, when RIIB deficient animals were given the protective IgG2a antibody a profound enhancement of the activity of this antibody was observed, as compared to mice wild-type for FcγRIIB. Quantitation of the tumor nodules in excised lungs revealed that wild-type, treated mice reduced tumor load by a factor of 3 (300 +/−30 compared to 100+/−10) while antibody treatment of RIIB−/− animals resulted in a 100-fold reduction (300 compared to 3). As shown previously, deletion of the activation γ subunit eliminates the in vivo protective effect of this antibody.

NK cells, a principal cell type involved in ADCC express the activation FcγR, RIII, but do not express the inhibitory counterpart, RIIB. Thus, the enhancement observed in RIIB deficient mice cannot be attributed to NK cell hyperresponsiveness. Rather, monocytes and macrophages, which express both RIII and RIIB, are therefore implicated as the dominant effector cell involved in this antibody-dependent protection in vivo. Thus the activity attributed to the protective IgG2a antibody in a wild-type animal represents the sum of the opposing activation and inhibitory pathways contributed by NK cells, monocytes and macrophages.

Anti-Tumor Activity of 4D5, HERCEPTIN®, and RITUXAN® Required FcγR Activating Receptors.

To determine the contribution of interactions between the Fc domain and effector cell FcγRs to the in vivo activity of HERCEPTIN® and RITUXAN®, the orthotopic athymic nude mouse tumor model was modified to generate a suitable model to address the role of FcγRII and RIII in the anti-tumor response. The common γ chain deficient mouse (FcRγ$^{-/-}$) (Takal T. et al., Cell, 1994, 76:519-29, which is incorporated herein by reference), lacking the activation FcγRs, I and III or the FcγRIIB deficient mouse (Takai, T. et al., Nature, 1996, 379:346-9, which is incorporated herein by reference) were each mated with athymic nude mice to generate FcRγ$^{-/-}$/nu/nu and FcγRIIB$^{-/-}$ /nu/nu mice for use in xenograft human tumor models. The anti-tumor activity of the anti-p185HER-2/neu antibody HERCEPTIN® (humanized IgG1) (Carter et al., 1992, supra) and its mouse parent antibody 4D5 (mouse IgG1) in preventing the growth of the human breast carcinoma BT474MI, which over-expresses p 185/HER-2/neu, was addressed in FcRγ$^{-/-}$ and +/+ athymic nude mice (FIGS. 1A-1D). Tumor growth, measured as volume, was identical in homozygous γ$^{-/-}$ and +/+ nu/nu mice injected subcutaneously with 5×10$^6$ BT474M1 cells. In γ$^{+/+}$ mice, a single 4 μg/gm intravenous dose, followed by weekly 2 μg/gm i.v. injections, resulted in near complete inhibition of tumor growth (tumor mass reductions of 90 and 96% in 4D5 and HERCEPTIN® treated mice) with only 4 of 17 mice developing palpable tumors. However, this protective effect of HERCEPTIN® and 4D5 was reduced in γ$^{-/-}$ mice. Tumor mass in antibody treated γ$^{-/-}$ mice were reduced by 29 and 44%, respectively and 14 of 15 mice developed palpable tumors.

Figure 1E:
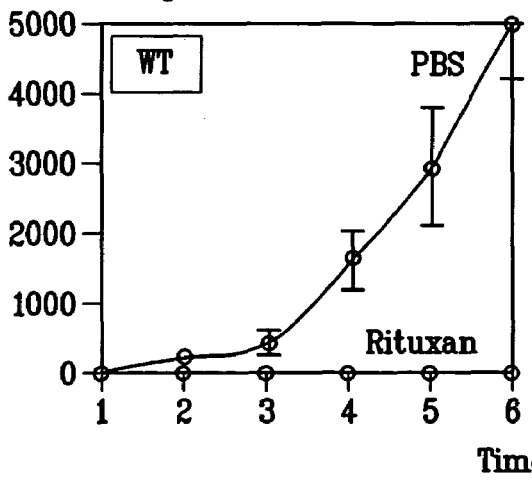
Figure 1F:
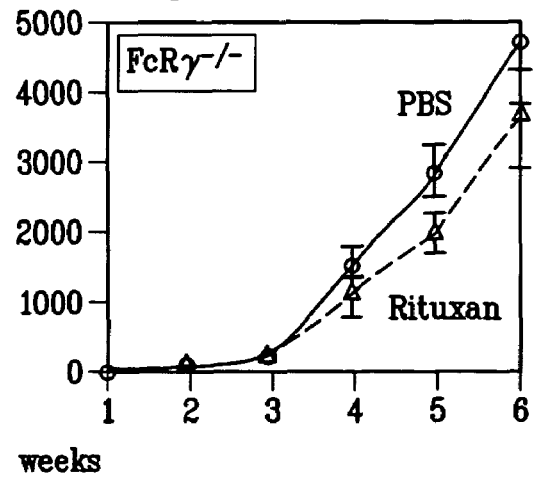

Similar results were obtained in the γ$^{-/-}$ nu/nu xenograft model on the mechanism by which the chimeric monoclonal IgG1 anti-CD20 antibody RITUXAN® inhibits B cell lymphoma growth in vivo. Tumor growth of the human B cell lymphoma cell line Raji is indistinguishable in γ$^{-/-}$ and +/+ nu/nu mice (FIGS. 1E and 1F). However, the protective effect of weekly i.v. doses of RITUXAN® (10 μg/gm) seen in γ$^{-/-}$ is reduced in γ$^{-/-}$ nu/nu mice. RITUXAN® treatment of wild-type athymic mice resulted in reductions of tumor mass by more than 99% and no wild type mice developed palpable tumors. In contrast, in γ$^{-/-}$ mice little protection was afforded by RITUXAN®; 6 of 7 mice developed palpable tumors and tumor mass reductions averaged just 23%.

Anti-Breast Tumor Activity of 4D5 and HER CEPTIN® is Enhanced in FcγRIIB Deficient Mice.

Figure 2A:
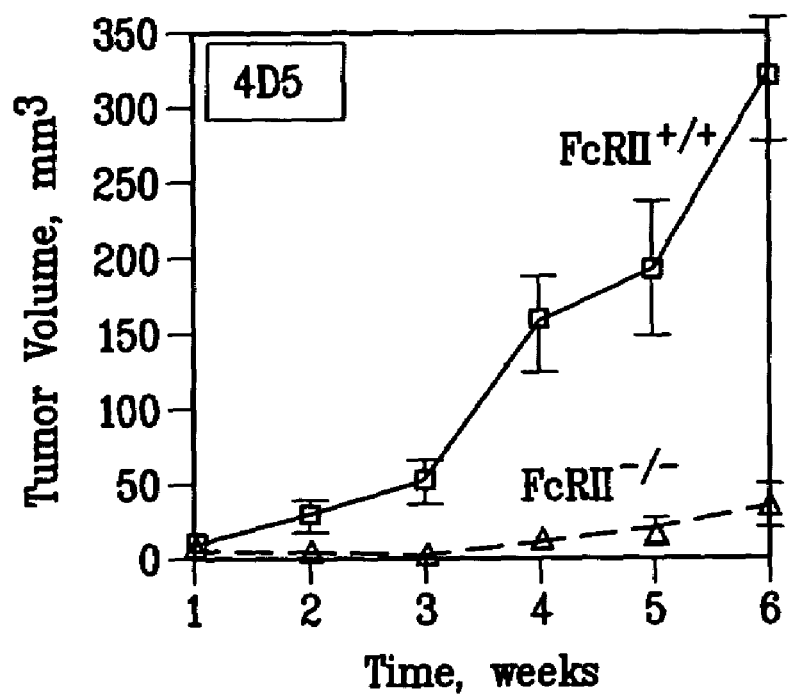
FIGS. 2A and 2B show that anti-breast tumor activity of 4D5 and HERCEPTIN® is enhanced in FcγRIIB deficient mice. Nude mice (8 per group) were injected with BT474M1 cells, as in FIG. 1, and treated with 0.4 μg/gm loading dose and 0.2 μg/gm weekly, a sub-therapeutic dose for wild-type mice. Complete inhibition is observed in RIIB deficient and partial inhibition in RIIB heterozygous mice.
Figure 2B:
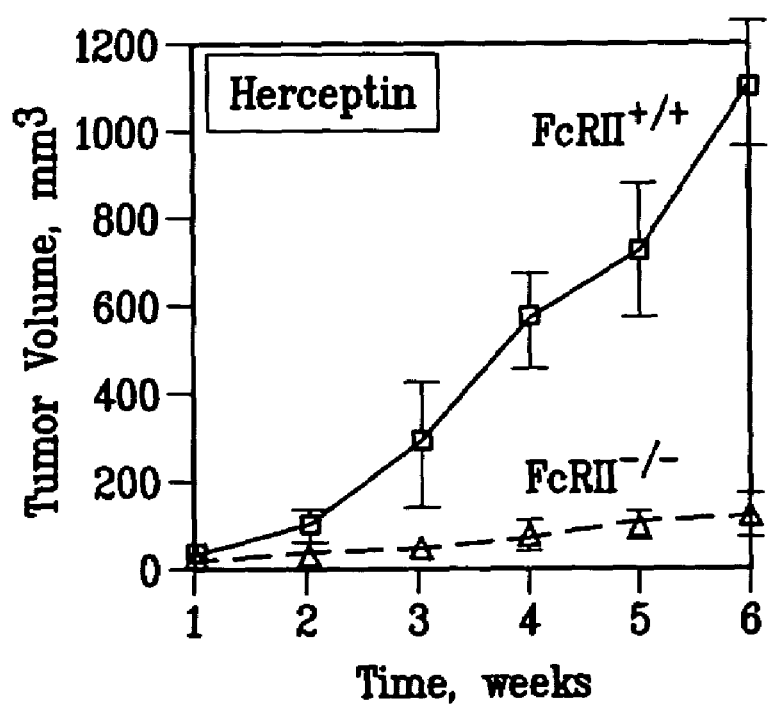

In contrast, FcγRIIB$^{-/-}$ mice were more effective at arresting BT474 growth in this nude mouse model (FIG. 2). At a sub-therapeutic dose of antibody (0.4 μg/gm loading, 0.2 μg/gm weekly) tumor growth in RIIB deficient mice was arrested, demonstrating the involvement of the inhibitory RIIB pathway in this model as well. Nude mice are known to display elevated NK cell numbers, leading to the presumption that antibody protection in those mice are not representative of the protection seen in syngenic systems, as in human disease. The observation that RIIB deletion enhances protection in nude mice indicates the involvement of effector cells other than NK cells, such as monocytes and macrophages in the protective response and further indicates that the FcR-dependent pathways are not restricted to an NK cell biased system but, as in the syngeneic melanoma system, is likely to be relevant in other syngeneic systems as well.

In Vitro and In Vivo Properties of D265a Mutant Antibody.

To further demonstrate the involvement of Fc-FcγR interactions in the protective response, a modification of the mouse IgG1 anti-HER2 antibody 4D5 was engineered to disrupt the ability of the antibody to engage cellular FcγR receptors while retaining its affinity for its cognate antigen p185 HER-2/neu. Based on alanine-scanning mutagenesis mapping of the murine IgG I Fc domain binding for FcγR, a single amino acid replacement at residue 265 in the $C_H2$ domain of the mouse IgG1 heavy chain was found to reduce binding of IgG1-containing immune complexes to both FcγRII and III in a receptor coated plate assay (FIG. 3A). This residue is located at a site within the Fc portion of the IgG molecule thought to interact directly with surfaces of FcRs. The 265 (asp→ala) mutation was placed in the 4D5 IgG1 heavy chain gene and transfected in parallel with the wild-type 4D5 IgG1 heavy chain into A293 cells along with the 4D5 kappa chain to produce 4D5 and mutant (D265A) antibodies. Since the mutation would not be expected to disrupt antibody-antigen interactions, as predicted, both 4D5 and D265A antibodies purified from transfected cell supernatants bound cellular p185HER-2/neu with equivalent avidity (FIG. 3E) and had comparable in vitro growth inhibitory activity when added to BT474M1 expressing breast carcinoma cells in tissue culture (FIG. 3B). However while D265A retained the wild-type characteristics of in vivo half-life, antigenic targeting and functional p185HER-2/neu receptor blockade, the in vitro ADCC capacity of the mutant was lost as a consequence of its reduced affinity for FcγRIII on effector cells (FIG. 3C). In vivo, the anti-tumor activity of D265A, when tested in the breast carcinoma BT474M1 xenograft model, displayed reduced anti-tumor activity as compared to 4D5 (FIG. 3D). Palpable tumors developed in all wild-type athymic mice treated with D265A while only in 2 of 5 mice treated with 4D5. D265A treatment reduced tumor volumes by 30% as compared to the 85% reduction seen with 4D5. The attenuated anti-tumor responses of D265A correlates with its impaired ability to activate FcR bearing effector cells despite its ability to inhibit tumor growth in vitro, supporting the conclusion that FcR engagement is a significant contributing component of anti-tumor activity in vivo.

Discussion

The data presented here suggest that FcγR binding contributes significantly to in vivo activity. This FcγR dependence appears to apply to more than a single antibody since it has been observed for both syngeneic and xenograft models for the three unrelated tumors and target antigens presented here. FcγR engagement involves both activation and inhibitory receptors and thus implicates monocytes and macrophages in the effector cell component of the protective response. Supportive evidence for this interpretation is found in the ability of HERCEPTIN® to mediate ADCC in vitro and the ability of anti-FcR antibodies to inhibit some of the in vivo activity of anti-CD20 antibodies (Funakoshi, S. et al., J. Immunother., 1996, 19:93-101, which is incorporated herein by reference). While the studies presented here demonstrate a significant role for Fc-FcγR interactions, triggering the growth and apoptotic regulatory pathways by antibody engagement of p185HER2/neu and CD20 may still contribute to the total in vivo efficacy of anti-tumor antibodies. Support for this interpretation can be seen in the partial protection observed in FcRγ$^{-/-}$ mice treated with anti-HER2/neu antibodies (FIG. 1), where the anti-tumor activity of these antibodies against the BT474M1 breast carcinoma cells is reduced but not ablated. Blocking signaling on tumor cells by antibodies may also act synergistically with immune effector responses by rendering the tumor cells more susceptible to immune effector cell triggered apoptotic or lytic cell death (Baselga, J. et al., Cancer Res., 1998, 58:2825-31, which is incorporated herein by reference). These studies highlight the fundamental importance of the inhibitory pathways in vivo and suggest that individual responses to anti-tumor antibodies may be dependent on expression of these inhibitory pathways.

Example 2

Generation of Variant IgG1 Fc Domains with Reduced Binding to FcRIIB

The underlying principle of Fc domain mutagenesis requires the expression of the dimeric Fc domain of human IgG1, for example, in a cellular system which glycosylates the molecule and displays it on the surface for binding studies. Compatible expression systems include eukaryotic cells such as yeast or mammalian cells.

In this example, yeast cells are employed as the host system. Error-prone PCR was employed to generate a library of sequences of the human IgG1 CH2-CH3 domain, according to procedures described previously (Saviranta et al., Prot. Eng., 1998, 11:143-152; Leung et al., Technique, 1992, 1:11) to generate an average of 2-4 amino acid changes per molecule. The primers employed spanned the hinge region (amino acids 218-229) and vector sequences flanking the 3' integration site in the expression vector pCT302. Libraries of greater than 10$^7$ recombinants were obtained. Expression was performed in the yeast AG1:AG2 surface display systems, as described (Boder and Wittrup, Nat. Biotechnol., 1997, 15:553-557, which is incorporated herein by reference) to generate an Fc fusion protein with the yeast parent Aga 2p, which is anchored to the yeast cell wall by disulfide interactions with the surface expressed yeast protein AG1. The PCR mutagenized IgG1 Fc fragment was cloned into the Aga2p-linker-fusion vector pCT302 and transformed into yeast strain EBY100. Transformants were selected on SD+CAA plates. Induction of expression of Aga2p Fc fusion was achieved by induction in galactose containing medium.

Screening of the mutant libraries was accomplished by panning or flow cytometry. For example, flow-cytometry screening was accomplished by FITC-labelled recombinant FcRIIB expressed as a hexameric complex, using a 1:1 molar ratio of FcRIIA/IgE Fc fusion and anti-IgE mAb E25 (Liu et al., Biochem., 1995, 34:10474, which is incorporated herein by reference) in the presence of an unlabelled 10-fold molar excess of FcRIIB/IgE anti-IgE complex. FITC positive yeast cells were enriched by multiple rounds of flow cytometry sorting and the resulting yeast cells plated and pCT302 fusion plasmid isolated and sequenced to determine the mutations generating reduced RIIB binding with unchanged or enhanced RIIA binding. Sites of differential interaction of IgG1 Fc with RIIA, RIIIA and RIIB were further defined by targeted PCR mutagenesis of those regions and repeating the yeast surface display screening to fully optimize binding differences. Similar experiments were performed to identify polypeptide variants with enhanced RIIB binding, RIIIA binding or RIIIB binding.

Alternatively, screening was also performed by panning of the mutagenized pCT302 fusion library on plates on to which recombinant RIIA, RIIB, RIIIA or RIIIB were immobilized. Multiple rounds of panning on RIIA were performed and the positive binders then panned on RIIB plates to remove any mutants which retain RIIB binding, thus identifying Fc mutants with retained or enhanced RIIA binding and reduced or eliminated RIIB binding.

Similar experiments can be performed using a mammalian expression vector for surface display on such cells and generating a mutagenized Fc library in an analogous manner.

Example 3

Isolation of a Monoclonal Antibody with Specificity for FcRIIB

A murine monoclonal antibody is obtained by immunizing mice with the recombinant human RIIB protein and spleen cells fused to obtain hybridomas, as described above. The resulting hybridomas are screened for diminished binding to RIIB, while not altering binding to RIIA or RIIIA or RIIIB. Antibodies with the desired properties are then cloned and the mRNA isolated and converted into cDNA for the heavy and light chains. A single chain Fv is then constructed as described above and expressed as a gene III fusion protein for phage display or Aga2p fusion for yeast display. A randomly mutagenized library is constructed for the single chain Fv binding and screening by panning for specificity in diminished affinity for RIIB over RIIA. The resulting phage or yeast cells are characterized by isolating the fusion phage genome or plasmid, respectively, DNA sequenced and then expressed as a recombinant antibody.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. Various patents, patent applications, and publications are cited herein, the disclosures of which are incorporated herein by reference in their entireties.

What is claimed is:

1. A method of enhancing cytotoxicity elicited by a therapeutic antibody in a subject, which method comprises disrupting activation of SHIP by Fc-gamma-receptor IIB (FcγRIIB) caused by binding of the antibody to FcγRIIB, wherein the disrupting is accomplished by modifying the Fc region of the antibody to reduce its affinity for FcγRIIB, thereby inhibiting binding of the antibody to FcγRIIB in the subject, wherein the Fc region of the antibody is at least 80% homologous with a native Fc region, and wherein said therapeutic antibody binds activating Fc-receptors with at least the same affinity as the wildtype antibody.

2. The method according to claim 1, wherein the antibody is an anti-tumor antibody.

3. The method according to claim 2, wherein the antibody is specific for a tumor cell growth receptor.

4. The method according to claim 3, wherein the antibody is specific for a HER2/neu growth factor receptor.

5. The method according to claim 1, wherein the antibody is specific for a CD20 B cell antigen.

6. The method according to claim 1, wherein the subject expresses human Fc receptors.

7. The method according to claim 1, wherein the wherein the Fc region of the antibody is at least 90% homologous with a native Fc region.

8. The method according to claim 1, wherein the wherein the Fc region of the antibody is at least 95% homologous with a native Fc region.

9. The method according to claim 1, wherein the wherein the Fc region of the antibody comprises 1 amino acid substitution compared to the native Fc region.

10. The method according to claim 1, wherein the wherein the Fc region of the antibody comprises 1-5 amino acid substitutions compared to the native Fc region.

11. The method according to claim 9, wherein the wherein the Fc region of the antibody consists of 1 amino acid substitution compared to the native Fc region.

12. The method according to claim 9, wherein the antibody is specific for a HER2/neu growth factor receptor.

13. The method according to claim 9, wherein the antibody is specific for a CD20 B cell antigen.

14. The method according to claim 1, wherein the wherein the Fc region of the antibody comprises 1 amino acid addition compared to the native Fc region.

15. The method according to claim 1, wherein the wherein the Fc region of the antibody comprises 1-5 amino acid additions compared to the native Fc region.

16. The method according to claim 14, wherein the wherein the Fc region of the antibody consists of 1 amino acid addition compared to the native Fc region.

17. The method according to claim 14, wherein the antibody is specific for a HER2/neu growth factor receptor.

18. The method according to claim 14, wherein the antibody is specific for a CD20 B cell antigen.

19. The method according to claim 1, wherein the wherein the Fc region of the antibody comprises at least 1 amino acid deletion compared to the native Fc region.

20. The method according to claim 19, wherein the wherein the Fc region of the antibody consists of 1 amino acid deletion compared to the native Fc region.

21. The method according to claim 19, wherein the antibody is specific for a HER2/neu growth factor receptor.

22. The method according to claim 19, wherein the antibody is specific for a CD20 B cell antigen.

23. A method of enhancing cytotoxicity elicited by a therapeutic antibody in a subject, which method comprises disrupting activation of SHIP by Fc-gamma-receptor IIB (FcγRIIB) caused by binding of the antibody to FcγRIIB, wherein the disrupting is accomplished by modifying the Fc region of the antibody to reduce its affinity for FcγRIIB, thereby inhibiting binding of the antibody to FcγRIIB in the subject wherein the Fc region of the antibody is at least 80% homologous with a native Fc region, and wherein said therapeutic antibody retains binding to FcRIIA and FcRIIIA.

24. The method of claim 23 wherein said retained binding is unchanged or enhanced as compared to the wildtype antibody.

25. A method of enhancing cytotoxicity elicited by a therapeutic antibody in a subject which method comprises disrupting activation of SHIP by Fc-gamma-receptor IIB (FcγRIIB) caused by binding of the antibody to FcγRIIB, wherein the disrupting is accomplished by modifying the Fc region of the antibody to reduce its affinity for FcγRIIB, thereby inhibiting binding of the antibody to FcγRIIB in the subject wherein the Fc region of the antibody is at least 80% homologous with a native Fc region, and wherein said therapeutic antibody that has reduced affinity for FcγRIIB has unchanged affinity for stimulatory FcRs, FcRI or FCRIII.

26. A method of enhancing cytotoxicity elicited by a therapeutic antibody in a subject, which method comprises disrupting activation of SHIP by Fc-gamma-receptor IIB (FcγRIIB) caused by binding of the antibody to FcγRIIB, wherein the disrupting is accomplished by modifying the Fc region of the antibody to reduce its affinity for FcγRIIB, thereby inhibiting binding of the antibody to FcγRIIB in the subject, wherein the Fc region of the antibody is at least 80% homologous with a native Fc region, and wherein said therapeutic antibody that has reduced affinity for FcγRIIB has enhanced affinity for stimulatory FcRs, FcRI or FCRIII.

27. The method according to claim 23, wherein the antibody is an anti-tumor antibody.

28. The method according to claim 23, wherein the antibody is specific for a tumor cell growth receptor.

29. The method according to claim 23, wherein the antibody is specific for a HER2/neu growth factor receptor.

30. The method according to claim 23, wherein the antibody is specific for a CD20 B cell antigen.

31. The method according to claim 23, wherein the subject expresses human Fc receptors.

32. The method according to claim 23, wherein the wherein the Fc region of the antibody is at least 90% homologous with a native Fc region.

33. The method according to claim 23, wherein the wherein the Fc region of the antibody is at least 95% homologous with a native Fc region.

34. The method according to claim 23, wherein the wherein the Fc region of the antibody comprises 1 amino acid substitution compared to the native Fc region.

35. The method according to claim 23, wherein the wherein the Fc region of the antibody comprises 1-5 amino acid substitutions compared to the native Fc region.

36. The method according to claim 23, wherein the wherein the Fc region of the antibody consists of 1 amino acid substitution compared to the native Fc region.

37. The method according to claim 23, wherein the wherein the Fc region of the antibody comprises 1 amino acid addition compared to the native Fc region.

38. The method according to claim 23, wherein the wherein the Fc region of the antibody comprises 1-5 amino acid additions compared to the native Fc region.

39. The method according to claim 23, wherein the wherein the Fc region of the antibody consists of 1 amino acid addition compared to the native Fc region.

40. The method according to claim 23, wherein the wherein the Fc region of the antibody comprises at least 1 amino acid deletion compared to the native Fc region.

41. The method according to claim 23, wherein the wherein the Fc region of the antibody consists of 1 amino acid deletion compared to the native Fc region.

\* \* \* \* \*